US012582323B2

(12) United States Patent
Miyagawa et al.

(10) Patent No.: US 12,582,323 B2
(45) Date of Patent: Mar. 24, 2026

(54) GUIDE WIRE CONNECTOR

(71) Applicant: NIPRO CORPORATION, Osaka (JP)

(72) Inventors: Katsuya Miyagawa, Osaka (JP);
Natsumi Shimazaki, Osaka (JP);
Tomoe Morita, Osaka (JP)

(73) Assignee: NIPRO CORPORATION, Settsu (JP)

( * ) Notice: Subject to any disclaimer, the term of this patent is extended or adjusted under 35 U.S.C. 154(b) by 0 days.

(21) Appl. No.: 18/140,785

(22) Filed: Apr. 28, 2023

(65) Prior Publication Data

US 2023/0263413 A1        Aug. 24, 2023

Related U.S. Application Data

(62) Division of application No. 16/318,820, filed as application No. PCT/JP2017/030930 on Aug. 29, 2017, now Pat. No. 11,707,200.

(30) Foreign Application Priority Data

Aug. 31, 2016    (JP) ................................. 2016-170383
Aug. 31, 2016    (JP) ................................. 2016-170384

(Continued)

(51) Int. Cl.
*A61B 5/0215*        (2006.01)
*A61B 5/00*        (2006.01)
(Continued)

(52) U.S. Cl.
CPC .......... *A61B 5/0215* (2013.01); *A61B 5/6851*
(2013.01); *H01R 13/11* (2013.01);
(Continued)

(58) Field of Classification Search
None
See application file for complete search history.

(56) References Cited

U.S. PATENT DOCUMENTS 3,513,430 A        5/1970    Heller
3,838,379 A        9/1974    Gieles et al.
(Continued)

FOREIGN PATENT DOCUMENTS

EP        0316763 A1        5/1989
EP        0925803 A2        6/1999
(Continued)

*Primary Examiner* — Meredith Weare
(74) *Attorney, Agent, or Firm* — Jordan and Koda, PLLC;
Steven P. Koda, Esq.

(57) ABSTRACT

A connector is provided with a holding component, a support component, a terminal electrically connected to a contact of a guide wire held by the holding component, and a guide component rotatable around an axial line of the guide wire with respect to the support component. The holding component is provided with a body having an insertion hole for the guide wire and a holding piece extending along an axial line of the insertion hole from the body and capable of being elastically deformed inward in a radial direction with respect to the axial line. The guide component has a guide surface guiding the holding piece inward in the radial direction. The holding component is slid along the axis line of the insertion hole with respect to the guide component, whereby the holding piece abuts on the guide surface to be elastically deformed inward in the radial direction.

9 Claims, 30 Drawing Sheets

(30)      Foreign Application Priority Data

Feb. 3, 2017    (JP) ................................. 2017-018408
Jun. 12, 2017   (JP) ................................. 2017-115312

(51) Int. Cl.
| | |
|---|---|
| *H01R 13/11* | (2006.01) |
| *H01R 13/502* | (2006.01) |
| *H01R 39/00* | (2006.01) |
| *H01R 43/20* | (2006.01) |
| *A61B 5/01* | (2006.01) |

(52) U.S. Cl.
CPC ........... *H01R 13/502* (2013.01); *H01R 39/00*
(2013.01); *H01R 43/20* (2013.01); *A61B 5/01*
(2013.01); *A61B 2562/0247* (2013.01); *A61B*
*2562/12* (2013.01); *A61B 2562/225* (2013.01)

(56)      References Cited

U.S. PATENT DOCUMENTS

| | | | |
|---|---|---|---|
| 4,023,562 A | 5/1977 | Hynecek et al. | |
| 4,886,070 A | 12/1989 | Demarest | |
| 5,078,831 A | 1/1992 | Miyazaki et al. | |
| 5,171,253 A | 12/1992 | Klieman | |
| 5,178,159 A * | 1/1993 | Christian | A61B 8/06 |
| | | | 600/585 |
| 5,271,415 A | 12/1993 | Foerster et al. | |
| 5,348,481 A | 9/1994 | Ortiz | |
| 5,412,993 A | 5/1995 | Ohtani | |
| 5,916,177 A | 6/1999 | Schwager | |
| 5,938,624 A | 8/1999 | Akerfeldt et al. | |
| 6,428,336 B1 * | 8/2002 | Akerfeldt | H01R 13/59 |
| | | | 439/805 |
| 7,124,639 B1 | 10/2006 | Kurtz | |
| 2004/0167442 A1 | 8/2004 | Shireman et al. | |
| 2004/0255682 A1 | 12/2004 | Petrova | |
| 2006/0074318 A1 * | 4/2006 | Ahmed | A61B 8/12 |
| | | | 600/561 |

| | | | |
|---|---|---|---|
| 2006/0264911 A1 * | 11/2006 | Nelson | A61M 39/12 |
| | | | 604/890.1 |
| 2007/0123826 A1 * | 5/2007 | Opie | A61B 17/00008 |
| | | | 604/165.01 |
| 2008/0294030 A1 * | 11/2008 | von Malmborg | A61B 5/061 |
| | | | 600/374 |
| 2009/0036754 A1 | 2/2009 | Pons | |
| 2011/0270230 A1 * | 11/2011 | Sage | A61M 39/1011 |
| | | | 604/533 |
| 2012/0104518 A1 | 5/2012 | Salmaso | |
| 2013/0045640 A1 | 2/2013 | Mahlin | |
| 2014/0066789 A1 | 3/2014 | Nishigishi | |
| 2014/0066790 A1 | 3/2014 | Burkett | |
| 2014/0120760 A1 * | 5/2014 | Zieman | H01R 12/91 |
| | | | 29/874 |
| 2014/0180142 A1 | 6/2014 | Millett | |
| 2016/0143616 A1 | 5/2016 | Okubo et al. | |
| 2016/0197429 A1 * | 7/2016 | Borkar | H01R 13/111 |
| | | | 439/733.1 |

FOREIGN PATENT DOCUMENTS

| | | |
|---|---|---|
| JP | 53-76880 U | 6/1978 |
| JP | 07-503163 A | 4/1995 |
| JP | 09-499 A | 1/1997 |
| JP | 11-178932 A | 7/1999 |
| JP | 2001-516938 A | 10/2001 |
| JP | 2002-542864 A | 12/2002 |
| JP | 2003-225312 A | 8/2003 |
| JP | 2003-525638 A | 9/2003 |
| JP | 2006-519072 A | 8/2006 |
| JP | 2010-540114 A | 12/2010 |
| JP | 2013-102845 A | 5/2013 |
| WO | 1998-043318 A1 | 10/1998 |
| WO | 2006-037082 A2 | 4/2006 |
| WO | 2011/134801 A1 | 11/2011 |
| WO | 2014/036477 A1 | 3/2014 |
| WO | 2014/188969 A1 | 11/2014 |

* cited by examiner

GUIDE WIRE CONNECTOR

CROSS REFERENCE TO RELATED APPLICATIONS

This a divisional application of U.S. patent application Ser. No. 16/318,820 titled "Pressure Measurement Device, Guide Wire Connector, Guide Wire, and Method for Manufacturing Guide Wire" filed by MIYAGAWA, Katsuya et al. on Jan. 18, 2019, which is a national stage application of PCT/JP2017/030930 filed on Aug. 29, 2017, the entire content of each of which are hereby incorporated by reference herein.

BACKGROUND OF THE INVENTION

The present invention relates to a guide wire connector with a sensor to be inserted into a blood vessel.

As a method for measuring the pressure of a fluid in a lumen of a living body, e.g., blood pressure in coronary arteries, a method including inserting a guide wire having a pressure sensor into a blood vessel is known. Patent Document 1 discloses a guide wire with a sensor in which a pressure detecting sensor chip is disposed inside a housing provided in a tip portion of the guide wire.

The above-described sensor chip is provided with a diaphragm containing a wafer and a piezoelectric resistance element provided in the diaphragm. To the diaphragm of the guide wire inserted into a blood vessel, blood pressure is applied. When the diaphragm is deflected by the blood pressure, the electrical resistance value of the piezoelectric resistance element varies. By the application of a current to the piezoelectric resistance element, the amount of a current flowing through the piezoelectric resistance element varies according to the blood pressure. The blood pressure is calculated based on the variation in the current amount.

In order to detect various kinds of physical quantities in a blood vessel, for example, blood pressure and blood temperature, a guide wire having a sensor is inserted into the blood vessel. The guide wire is inserted into a vein from a lower portion of the collarbone or the thigh, and is sent out so as to reach coronary arteries, for example.

In order to calculate the physical quantities, such as blood pressure and blood temperature, in a calculation device based on data obtained by the sensor, the guide wire is electrically communicatively connected to the calculation device through a connector. On the end of the guide wire, a contact is provided and the connector is provided with terminals. The shape of the contact is generally a cylindrical shape. In a connector described in Patent Document 2, terminals are a pair of plate springs disposed facing each other. In a state where the guide wire is inserted into the connector, the contact of the cylindrical shape is held between the pair of plate springs. Thus, the contact of the guide wire is electrically connected to the terminals of the connector.

In order to detect various kinds of physical quantities in a blood vessel, e.g., blood pressure and blood temperature, a guide wire having a sensor is inserted into a blood vessel. The guide wire is inserted into a vein from a lower portion of the collarbone or the thigh, and then the tip thereof is sent to coronary arteries, for example. Then, the blood pressure in the coronary arteries is measured by the sensor provided on the tip of the guide wire.

Based on an electric signal output from the sensor, the physical quantities, such as blood pressure and blood temperature, are calculated in the calculation device. Therefore, the guide wire is connected to the calculation device so as to be able to communicate the electric signal through a female type connector and a cable. Power is supplied to the sensor from the calculation device. A male type connector which can be inserted into the female type connector is provided at the proximal end of the guide wire. The male type connector is provided with a plurality of electrodes, for example. The electrodes and the sensor are connected by conductive wires which are inserted into and passed through the internal space of the guide wire (see Patent Document 3). In each of the conductive wires, the electric signal output from the sensor is transmitted or power is supplied to the sensor.

PATENT LITERATURE

Patent Document 1: Japanese Unexamined Patent Application Publication (Translation of PCT Application) No. 2010-540114

Patent Document 2: Japanese Unexamined Patent Application Publication (Translation of PCT Application) No. 2001-516938

Patent Document 3: Japanese Unexamined Patent Application Publication No. 2003-225312

SUMMARY OF THE INVENTION

In order to increase the blood pressure measurement accuracy, the gain (input/output ratio of voltage or current) of the sensor is desirably large. On the other hand, it is not desirable to increase the size of the sensor for an increase of the gain.

When the guide wire is moved forward and backward within a blood vessel, the guide wire is rotated. By rotating the guide wire, the tip of the guide wire which is configured to be easy to curve rotates. The direction of the tip of the curved guide wire is changed around the axis of the guide wire. This makes it easy to advance the tip of the guide wire into a target blood vessel in a branch portion of a blood vessel, for example.

In the connector described in Patent Document 2, the terminals are the pair of plate springs disposed facing each other as described above. The guide wire held by the pair of plate springs can move in the radial direction with respect to the central axis of the guide wire while rotating with the rotation of the guide wire.

In a direction where the pair of plate springs faces each other, even when the guide wire moves, the pair of plate springs moves following the movement of the guide wire. However, in a direction orthogonal to the direction where the pair of plate springs faces each other, the pair of plate springs does not follow the movement of the guide wire. Therefore, when the guide wire also moves in the direction orthogonal to the direction where the pair of plate springs faces each other, the electrical connection between the contact and the terminal is momentarily cut or a contact portion between the contact and the terminal shifts. As a result, a jump or a drift may arise in the electric signal transmitted to the calculation device from a sensor.

In general, the outer diameter of the guide wire is sufficiently smaller than 1 mm, and therefore the inner diameter of the internal space of the guide wire which the conductive wire is inserted into and passed through is similarly small. On the other hand, it is desirable that the conductive wires are not exposed to the outside from the guide wire from the viewpoint of preventing the breakage of the conductive wires. Therefore, the conductive wires and the electrodes are connected in the internal space of the male type connector of the guide wire but the connection operation tends to be complicated.

The present invention has been made in view of the above-described circumstances. It is an object of the present invention to provide a pressure measurement device capable of achieving an increase of the gain of a sensor.

It is another object of the present invention to provide a guide wire connector in which the electrical connection between a contact and a terminal is hard to be cut.

It is still another object of the present invention to provide a guide wire in which a conductive wire inserted into and passed through the internal space of the guide wire and an electrode of a connector are easily electrical connected and a method for manufacturing the guide wire.

(1) A guide wire connector according to the present invention is provided with a holding portion holding a guide wire, a support portion supporting the holding portion rotatably around an axis line of the guide wire held by the holding portion, a terminal electrically connected to a contact of the guide wire held by the holding portion, and a guide portion rotatable around the axis line of the guide wire with respect to the support portion. The holding portion is provided with a body having an insertion hole for the guide wire and a holding piece extending along an axis line of the insertion hole from the body and capable of being elastically deformed inward in a radial direction with respect to the axis line. The guide portion has a guide surface guiding the holding piece inward in the radial direction. The holding portion is slid along the axis line of the insertion hole with respect to the guide portion, whereby the holding piece abuts on the guide surface to be elastically deformed inward in the radial direction.

According to the above-described configuration, the holding portion is slid along the axis line of the insertion hole with respect to the guide portion, whereby the holding piece abuts on the guide surface to be elastically deformed inward in the radial direction. As a result, the guide wire is held by the holding piece. When slid in the opposite direction, the holding piece is separated from the guide surface, so that the hold of the guide wire is released. Therefore, the guide wire is held or the hold is released by sliding the holding portion.

(2) Preferably, the support portion is provided with a lock portion locking the slide of the holding portion at a position where the holding piece abuts on the guide surface and enabling the holding piece to rotate around the axis line of the guide wire, the holding portion is provided with a hook portion integrally molded with the body and capable of being elastically deformed inward in the radial direction, recessed portion is formed in a proximal end portion of the hook portion, and the recessed portion can be engaged with the lock portion.

According to the above-described configuration, the recessed portion is engaged with the lock portion of the support portion, whereby the relative movement of a holding component along the axis line with respect to the connector body is regulated.

(3) Preferably, the holding portion is provided with a fitting portion abutting on the guide portion to be fitted thereto at the position where the holding piece abuts on the guide surface and the guide portion is provided with a fitting target portion to be fitted to the fitting portion.

According to the above-described configuration, when the holding piece abuts on the guide surface, the fitting portion is fitted to a fitting target portion to abut thereon even in a state where the lock portion is not engaged with the recessed portions, so that the movement of the holding component to the proximal side of a support component.

(4) Preferably, the terminal has at least three terminal portions disposed around the axis line of the guide wire held by the holding portion and the three terminal portions individually abut on the contact while being elastically displaced outward in a radial direction of the guide wire held by the holding portion.

(5) Preferably, an angle $\theta$ around the axis line of the guide wire between two adjacent terminal portions satisfies a relationship of $90°<\theta<180°$.

According to the above-described configuration, with respect to the angle $\theta$ around the axis line of the guide wire between the two adjacent terminal portions, the at least three terminal portions disposed around the axis line of the guide wire are provided. Therefore, even when the contact moves in the radial direction so that the axis line of the guide wire shifts, each of the terminal portions follows the movement of the contact by the elastic deformation of the terminal portions. Therefore, a trouble that the electrical connection between the contact and the terminal is momentarily cut is hard to occur. Preferably, the angle $\theta$ satisfies the relationship of $90°<\theta<180°$.

(6) More preferably, the angle $\theta$ satisfies the relationship of $\theta=120°$.

According to the above-described configuration, the angle $\theta$ satisfies the relationship of $\theta=120°$, and therefore the three terminal portions are disposed at equal intervals. Therefore, even when the guide wire moves in any direction of the radial directions, each of the terminal portions follows the contact. Therefore, the trouble that the electrical connection between the contact and the terminal is momentarily cut is more difficult to occur.

(7) Preferably, each of the terminal portions has a contact surface facing the contact of the guide wire and the contact surface has a cross section along the axis line of the guide wire held by the holding portion of a curved shape protruding inward in the radial direction of the guide wire.

According to the above-described configuration, each of the terminal portions point-contacts the contact along the axis line of the guide wire. Therefore, when the guide wire moves along the axis line, each of the terminal portions easily retreats in a direction of separating from the axis line. Therefore, the guide wire can be easily inserted into and removed from the connector.

(8) Preferably, each of terminal portions is a plate spring and the terminal has a shape in which each of both ends in a direction along the axis line of the guide wire in each of the plate springs integrally continues in a cylindrical shape along the circumferential direction.

(9) Preferably, the terminal is provided with a body in which one end in a direction along the axis line of the guide wire in each of the plate springs integrally continues in a cylindrical shape along the circumferential direction and a converging tube externally fitted to the other end of each of the plate springs and capable of being elastically deformed so as to enlarge the diameter.

According to the above-described configuration, the converging tube is externally fitted to the other end of each of the plate springs and capable of being elastically deformed so as to enlarge the diameter. The plate spring which is the terminal portion is subject to not only the energization force of the plate spring itself but the energization force caused by a tubular spring. Therefore, the energization force of the terminal portions is easily adjusted.

(10) A guide wire according to the present invention has a tubular body, a conductive wire which is inserted into and passed through the internal space of the body to be extended from a proximal end portion of the body, and a connector having a tubular shape and having an electrode ring exposed to the outer peripheral surface of the tubular shape and an electrode pin connected to the electrode ring and extended from a distal end portion through the internal space of the tubular shape to be connected to the conductive wire in the distal end portion.

According to the above-described configuration, a distal end portion of the electrode pin and the conductive wire are easily connected even when the electrode ring and the electrode pin are assemblies beforehand.

(11) Preferably, the guide wire has two or more of the conductive wires, two or more of the electrode rings located apart from each other in an axial direction, and two or more of the electrode pins connected to the two or more of the electrode rings, in which the conductive wires and the electrode pins are connected in one-to-one correspondence.

(12) Preferably, the electrode pins are disposed at different positions in the circumferential direction in the internal space of a connector.

The strength of the connector is held due to the fact that the electrode pins are bundled in the internal space of the electrode rings.

(13) Preferably, distal end portions of the electrode pins are disposed at different positions in the axial direction in the internal space of the connection tube.

According to the above-described configuration, the connection relationship between each of the electrode pins and each of the electrode rings can be grasped based on the positions of the distal end portions.

(14) Preferably, the electrode pins each have an insulation coated outer periphery and conduction portions not having the insulation coat at the distal end portion and a position corresponding to the electrode ring to be connected, in which the electrode pins are individually connected to the conductive wires and the electrode rings in the conduction portions and the conduction portions of the electrode pins do not overlap in the axial direction.

According to the above-described configuration, a short circuit between the conduction portions of the electrode pin can be suppressed.

(15) Preferably, the guide wire further has a connection tube covering the conductive wires and the electrode pins and connecting the proximal end portion of the body and the distal end portion of the connector.

The connection tube covering connection portions of the conductive wires and the electrode pins is configured as a separate body from the body and the connector. Therefore, there is no member covering the connection portions of the conductive wires and the electrode pins in a state where the connection tube is not connected to the body and the connector, and thus the workability is good.

(16) Preferably, the body has a tapered portion in which the outer diameter decreases toward the proximal end and a small-diameter portion extended from the tapered portion to the proximal end, in which the connection tube is movable in the axial direction with respect to the small-diameter portion in a state of being externally fitted to the small-diameter portion.

By the movement of the connection tube in the axial direction with respect to the small-diameter portion, the connection portions between the conductive wires and the electrode pins are exposed to the outside or covered. Moreover, due to the fact that the connection tube is externally fitted to the small-diameter portion, the outer diameter of the connection tube can be made small.

(17) Preferably, the connection tube contains a conductive material and is electrically connected to the body.

According to the above-described configuration, the body can be easily grounded through the connection tube.

(18) Preferably, the guide wire further has an electronic component which is located in a distal end portion of the body to be connected to the conductive wires and outputs an electric signal according to the physical quantity of a fluid.

(19) A method for manufacturing a guide wire according to the present invention includes a first process of electrically connecting a conductive wire inserted into and passed through the internal space of a tubular body to be extended from a proximal end portion of the body and an electrode pin connected to an electrode ring provided in a tubular connector and extended from a distal end portion through the internal space of the connector and a second process of connecting a connection tube to the proximal end portion of the body and the distal end portion of the connector while covering the conductive wire and the electrode pin.

According to the above description, in a state where the connection tube is not connected to the body and the connector, there is no member covering a connection portion of the conductive wire and the electrode pin, and thus the workability is good.

(20) Preferably, in the first process, the connection tube is brought into an externally fitted state of being externally fitted to the body or the connector, and then the conductive wire and the electrode pin are electrically connected and, in the second process, the connection tube in the externally fitted state is moved in a direction of projecting in an axial direction from the proximal end portion of the body or a direction of projecting in the axial direction from the distal end portion of the connector.

By the movement of the connection tube from the externally fitted state with respect to the body or the connector, the connection portion between the conductive wire and the electrode pin is exposed to the outside or covered

(21) A pressure measurement device according to the present invention is provided with a guide wire having flexibility and capable of being inserted into a lumen of a living body and a sensor provided in the guide wire, in which the guide wire has a cylindrical housing accommodating the sensor and the sensor has a sensor body having a distal end surface facing the distal side in an axial direction of the guide wire, a diaphragm disposed on the distal end surface, a bridge circuit disposed on the distal end surface and surrounding the diaphragm, and four conductive wires connected to the bridge circuit. The bridge circuit is provided with four resistors which are fixed to an outer peripheral portion of the diaphragm and in which an electrical resistance value varies with elastic deformation of the diaphragm and four terminals connected to the four resistors and the four conductive wires.

According to the above-described configuration, the four resistors are fixed to the outer peripheral portion of the diaphragm. Therefore, when the diaphragm is elastically deformed by the pressure of a fluid in a lumen, the electrical resistance values of the four resistors individually vary. Therefore, the gain of the sensor increases.

(22) Preferably, space is formed on the distal side relative to the distal end surface of the sensor.

According to the above-described configuration, a vibration caused by the contact between a distal end portion of the guide wire and the wall surface in a lumen is difficult to be transmitted to the sensor, and therefore the detection accuracy of the sensor becomes high. Furthermore, due to the fact that a tip guide portion, a spiral body, and the like are provided on the distal side relative to the space, the contact with the wall surface in the lumen is further buffered and the vibration is difficult to be transmitted to the sensor, and therefore the detection accuracy of the sensor becomes higher.

(23) Preferably, the shape of the diaphragm is a disk shape.

According to the above-described configuration, the shape of the diaphragm is the disk shape. Therefore, when the diaphragm is elastically deformed, the deformation amount of an outer peripheral portion of the diaphragm is uniform irrespective of positions in the circumferential direction. The variation amount of the electrical resistance value of the resistor is proportional to the deformation amount of the diaphragm at the position where the resistor is fixed. Therefore, even when the position of the resistor with respect to the diaphragm somewhat shifts due to variations in manufacturing and the like, for example, the resistance variation characteristics of the resistors, i.e., the variation amount of the electrical resistance value to pressure variation, do not sharply fluctuate. In the four resistors, the resistance variation characteristics are kept uniform, and therefore a fluctuation of the gain of the sensor due to the variations in manufacturing is small.

(24) Each of the terminals is disposed between two adjacent resistors among the four resistors.

According to the above-described configuration, each terminal is disposed between the two adjacent resistors. Therefore, the path length of the bridge circuit is shortened as compared with a case where each terminal is disposed at a position deviated from the position between the two resistors. Thus, a small reduction of the sensor is achieved.

(25) The sensor body has a proximal end surface facing the proximal side in the axial direction, four through-holes opened to the distal end surface and the proximal end surface and formed along the axial direction, and four electroconductive layers individually laminated around an opening of each of the four through-holes of the distal end surface, in which the terminals are the electroconductive layers.

According to the above-described configuration, each of the conductive wires is connected to a portion laminated on the distal end surface of the sensor body of each electroconductive layer. Therefore, no conductive wires are disposed on the outer peripheral surface of the sensor body.

(26) Preferably, the sensor is provided with a coating member partially covering the four electroconductive layers and the four conductive wires and covering at least connection portions between the electroconductive layer and the conductive wires.

According to the above-described configuration, a fluid in a lumen does not contact the connection portion. Therefore, a degradation of the connection portion is suppressed and the connection portion is waterproofed and insulated.

(27) Preferably, the guide wire is provided with a core wire and a tapered pin fixed to a distal end portion of the core wire, in which the tapered pin is connected to the coating member.

The pressure measurement device of the present invention can achieve an increase in the gain of the sensor.

Moreover, according to the present invention, a trouble that the electrical connection between the contact and the terminal is momentarily cut is difficult to occur.

Moreover, the present invention facilitates the electrical connection between the conductive wire inserted into and passed through the internal space of the guide wire and the electrode of the connector.

BRIEF DESCRIPTION OF DRAWINGS

FIG. 13(A) is a cross-sectional view along the cut line VIA-VIA of FIG. 4 and FIG. 13(B) is a cross-sectional view along the cut line VIB-VIB.

FIG. 14(A) is a cross-sectional view along the cut line VIA-VIA of FIG. 11 and FIG. 14(B) is a cross-sectional view along the cut line VIB-VIB.

FIG. 17(A) is a front view, FIG. 17(B) is a top view, FIG. 17(C) is a side view, and FIG. 17(D) is a developed view.

FIG. 18(A) is a cross-sectional view of the terminal of the connector according to the second embodiment of the present invention and FIG. 18(B) and FIG. 18(C) are cross-sectional views of a contact between the terminal of the connector and a guide wire according to the second embodiment of the present invention.

DETAILED DESCRIPTION OF THE INVENTION

Hereinafter, preferable embodiments of the present invention are described. It is a matter of course that the embodiments are merely exemplary of the present invention and the embodiments can be altered in the range where the gist of the present invention is not altered.

Configuration of First Embodiment

<Pressure Measuring Device 10>

Figure 1:
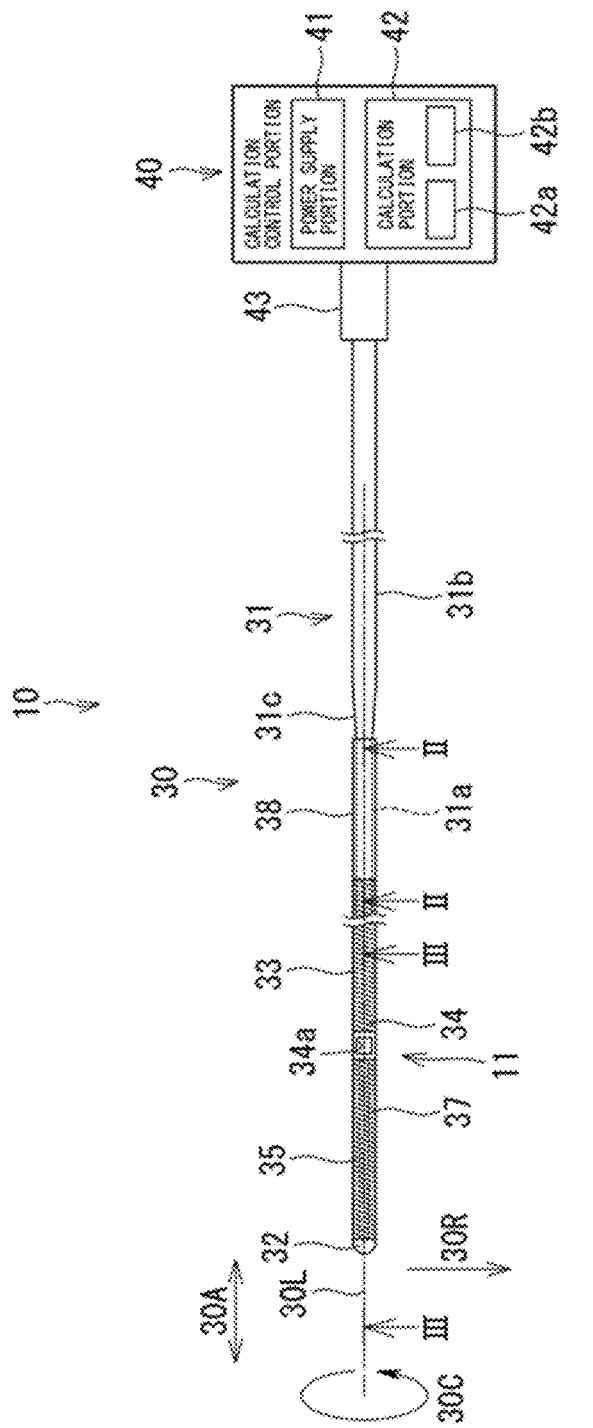
FIG. 1 is a schematic view of a pressure measurement device according to a first embodiment of the present invention.

As illustrated in FIG. 1, a pressure measurement device 10 according to a first embodiment is provided with a guide wire 30 and a pressure sensor 11 provided in the guide wire 30. To one end of the guide wire 30, a calculation control portion 40 is electrically connected. In FIG. 1, a fixed end (end connected to the calculation control portion 40) is a proximal end (right side in FIG. 1) of both ends of the guide wire 30 and a free end (tip when inserted into a blood vessel) thereof is a distal end (left side in FIG. 1). Hereinafter, in the guide wire 30, the side where the proximal end is present is defined as a proximal side and the side where the distal end is present is defined as a distal side.

Figure 2:
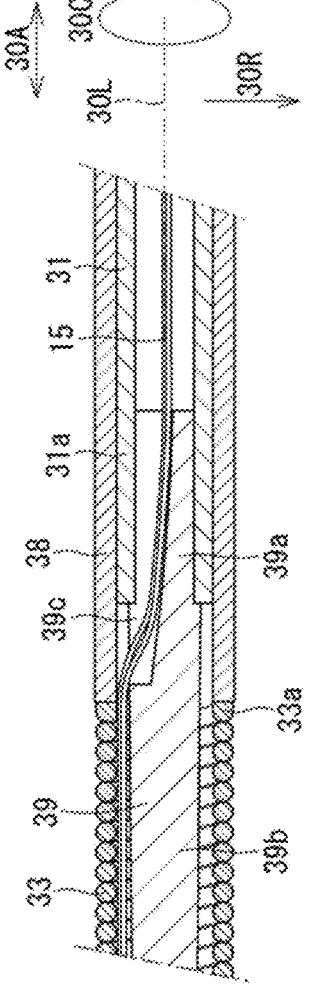
FIG. 2 is an enlarged cross sectional view along the cut line II-II of FIG. 1.
Figure 3:
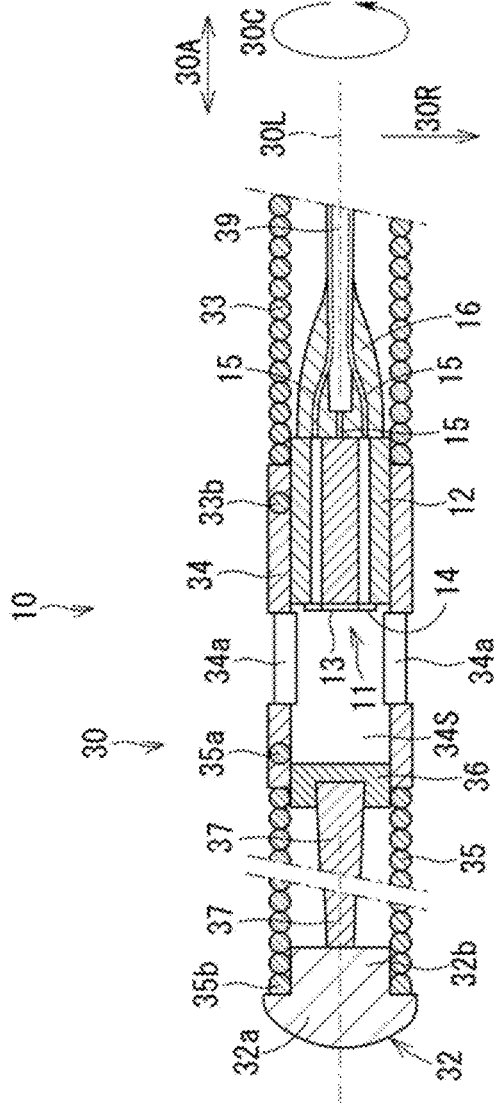
FIG. 3 is an enlarged cross sectional view along the cue line III-III of FIG. 1.

The guide wire 30 is a long and narrow cable and can be inserted into blood vessels (example of the lumen of a living body), such as coronary arteries. The pressure sensor 11 is provided in an end portion on the distal side of the guide wire 30. The calculation control portion 40 calculates the blood pressure (example of the pressure of the fluid in a lumen) based on electric information (voltage value) to be output from the pressure sensor 11. More specifically, the pressure measurement device 10 is used for the measurement of the blood pressure. FIG. 1 to FIG. 3 illustrate an axial center line 30L of the guide wire 30. In this specification, directions relating to components configuring the guide wire 30, i.e., an axial direction 30A, a radial direction 30R, and a circumferential direction 30C, are defined as follows. The axial direction 30A, the radial direction 30R, and the circumferential direction 30C are defined based on the axial center line 30L in a state where the guide wire 30 is in a straight state without being deflected or curved, i.e., the axial center line 30L which is a straight line. The axial direction 30A is a direction parallel to the axial center line 30L and including both the distal direction and the proximal direction. The radial direction 30R includes all directions orthogonal to the axial center line 30L. The circumferential direction 30C is a direction around the axial center line 30L.

<Guide Wire 30>

As illustrated in FIG. 1, the guide wire 30 is provided with a core wire 31, a tip guide portion 32, a first spiral body 33, a housing 34, a second spiral body 35, and a guide tube 38. As illustrated in FIG. 2, the guide wire 30 is provided with a tapered pin 39. As illustrated in FIG. 3, the guide wire 30 is provided with a connection wall 36 and a tip wire 37.

As illustrated in FIG. 1, the core wire 31 is a member configuring the skeleton of the guide wire 30. The core wire 31 gives fixed mechanical strength to the curving of the guide wire 30 so that the guide wire 30 can be inserted into a blood vessel without being crooked. The core wire 31 is a cylindrical wire rod and extends from the proximal end to the distal side. The material of the core wire 31 is medical stainless steel, for example. The axial center line of the core wire 31 is parallel to the axial center line 30L.

In the core wire 31, the distal side is easier to deflect than the proximal side. The core wire 31 has a small-diameter portion 31a located on the distal side, a large-diameter portion 31b located on the proximal side, and a tapered portion 31c connecting the small-diameter portion 31a and the large-diameter portion 31b. The small-diameter portion 31a and the large-diameter portion 31b each have a fixed outer diameter. The outer diameter of the large-diameter portion 31b is larger than the outer diameter of the small-diameter portion 31a. The outer diameter of the tapered portion 31c is equal to the outer diameter of the large-diameter portion 31b in the proximal end, gradually decreases toward the distal end from the proximal end, and is equal to the outer diameter of the small-diameter portion 31a in the distal end. Due to the fact that the outer diameter of the core wire 31 gradually decreases toward the distal side, the rigidity of the core wire 31 decreases in order of the large-diameter portion 31b, the tapered portion 31c, and the small-diameter portion 31a.

As illustrated in FIG. 2, the tapered pin 39 is disposed from a distal end portion of the core wire 31 on the distal side. The tapered pin 39 is also a member configuring the skeleton of the guide wire 30 as with the core wire 31 and gives fixed mechanical strength to the curving of the guide wire 30.

The tapered pin 39 is provided with a shaft portion 39a located on the proximal side and a tapered portion 39b extending from the shaft portion 39a to the distal side. The outer diameter of the shaft portion 39a is constant. The shaft portion 39a is inserted into the small-diameter portion 31a of the core wire 31. The shaft portion 39a is fixed to the small-diameter portion 31a by laser welding or an adhesive, for example. The outer diameter of the tapered portion 39b is formed to be tapered toward the distal side. Therefore, the rigidity of the tapered portion 39b gradually decreases toward the distal side. A distal end portion of the guide wire 30 where the tapered pin 39 is disposed is easy to bend, and therefore the guide wire 30 is easily guided along a blood vessel. Moreover, a slot 39c opened to the outer peripheral surface of the tapered pin 39 is formed in parallel to the axial direction 30A from the proximal end of the tapered pin 39 to a proximal side portion of the tapered portion 39b. Four conductive wires 15 (described later) of the pressure sensor 11 pass through the inside of the core wire 31 via the slot 39c to be connected to the calculation control portion 40.

As illustrated in FIG. 1 and FIG. 2, the guide tube 38 is located on the outside in the radial direction 30R of the small-diameter portion 31a of the core wire 31 and covers a proximal side portion of the small-diameter portion 31a. The shape of the guide tube 38 is a cylindrical shape. The axial center line of the guide tube 38 is parallel to the axial center line 30L. The guide tube 38 is fixed to the outer peripheral surface of the small-diameter portion 31*a* of the core wire 31. The guide tube 38 has flexibility. The guide tube 38 contains medical synthetic resin, for example, and is thermally fused to the outer peripheral surface of the core wire 31, for example.

As illustrated in FIG. 1 and FIG. 3, the tip guide portion 32 is disposed at the distal end of the guide wire 30. The tip guide portion 32 is a portion abutting on a blood vessel wall when the guide wire 30 is inserted into a blood vessel to thereby guide the movement direction of the guide wire 30 along the blood vessel. The tip guide portion 32 is provided with a hemispherical portion 32*a* located on the distal side and a columnar portion 32*b* extending from the hemispherical portion 32*a* to the proximal side. The hemispherical portion 32*a* has a hemispherical shape projecting to the distal side so as not to damage the blood vessel wall. The outer diameter of the hemispherical portion 32*a* is almost equivalent to the outer diameter of the second spiral body 35. The columnar portion 32*b* has a cylindrical shape projecting from the hemispherical portion 32*a* to the proximal side and having an outer diameter smaller than the outer diameter of the hemispherical portion 32*a*. The columnar portion 32*b* is inserted into the second spiral body 35, whereby the tip guide portion 32 is positioned with respect to the second spiral body 35, so that the outer surfaces of the hemispherical portion 32*a* and the second spiral body 35 smoothly continue without a level difference. The material of the tip guide portion 32 is medical stainless steel, for example.

As illustrated in FIG. 1 and FIG. 3, the first spiral body 33 and the second spiral body 35 are provided on the distal side of the guide wire 30. The first spiral body 33 and the second spiral body 35 have bending rigidity lower than that of the tapered pin 39, i.e., easy to bend. The first spiral body 33 is configured by a spirally wound wire rod. The material of the first spiral body 33 is medical stainless steel, for example. The axial center line of the first spiral body 33 is parallel to the axial center line 30L. As illustrated in FIG. 2, the tapered portion 39*b* of the tapered pin 39 is inserted into the first spiral body 33. The first spiral body 33 has a proximal end portion 33*a* (FIG. 2) and a distal end portion 33*b* (FIG. 3). As illustrated in FIG. 2, the proximal end portion 33*a* is fixed to the outer peripheral surface of the tapered portion 39*b* of the tapered pin 39 by laser welding or an adhesive, for example. Thus, the bending rigidity of the first spiral body 33 is reinforced with the tapered pin 39.

As illustrated in FIG. 1 and FIG. 3, the housing 34 is a casing accommodating the pressure sensor 11 in an internal space 34S thereof. The housing 34 has a cylindrical shape and has the internal space 34S. The material of the housing 34 is medical stainless steel, for example. The axial center line of the housing 34 is parallel to the axial centerline 30L. In a proximal end portion of the housing 34, the distal end portion 33*b* of the first spiral body 33 is fixed by laser welding or an adhesive, for example.

The housing 34 has a plurality of through-holes 34*a*. In the first embodiment, the housing 34 has two through-holes 34*a*. The through-holes 34*a* penetrate a cylindrical wall of the housing 34 along the radial direction 30R. The internal space 34S of the housing 34 and the outside communicate with each other through the through-holes 34*a*. The two through-holes 34*a* are disposed along the circumferential direction 30C of the guide wire 30 at a 180° interval around the axial center line 30L.

The second spiral body 35 is configured by a spirally wound wire rod. The material of the second spiral body 35 is medical stainless steel, for example. The axial center line of the second spiral body 35 is parallel to the axial center line 30L. The second spiral body 35 has a proximal end portion 35*a* and a distal end portion 35*b*. The proximal end portion 35*a* of the second spiral body 35 is fixed to a distal end portion of the housing 34. The second spiral body 35 and the housing 34 are fixed by laser welding or an adhesive, for example. The columnar portion 32*b* of the tip guide portion 32 is inserted into the distal end portion 35*b* of the second spiral body 35. The distal end portion 35*b* is fixed to the outer peripheral surface of the columnar portion 32*b*. The second spiral body 35 and the tip guide portion 32 are fixed by laser welding or an adhesive, for example.

The connection wall 36 is a member for connecting the tip wire 37 to the housing 34. The connection wall 36 is fixed to the distal end portion of the housing 34. The connection wall 36 is configured by a metal soldering material, for example.

The tip wire 37 reinforces the bending rigidity of the second spiral body 35. The tip wire 37 is a wire rod containing medical stainless steel, for example. The axial center line of the tip wire 37 is parallel to the axial center line 30L. A proximal end portion of the tip wire 37 is fixed to the connection wall 36. A distal end portion of the tip wire 37 is fixed to the columnar portion 32*b* of the tip guide portion 32 by laser welding or an adhesive, for example.

According to the configuration described above, the tapered pin 39 and the tip guide portion 32 are connected through the first spiral body 33, the housing 34, and the second spiral body 35. The housing 34 and the tip guide portion 32 are connected through the tip wire 37. The tapered pin 39 is fixed to the core wire 31. Thus, the guide wire (except the core wire 31) 30 itself is supported by the core wire 31 and mechanical strength is given thereto.

According to such a configuration, when an operation of sending out the guide wire 30 to a blood vessel in the proximal end is performed, the guide wire 30 progresses in the blood vessel without being crooked following the operation. When the tip guide portion 32 contacts the blood vessel wall, the guide wire 30 is curved along the blood vessel wall.

<Pressure Sensor 11>

As illustrated in FIG. 3, the pressure sensor 11 is disposed in the internal space 34S of the housing 34. A proximal side portion of the internal space 34S is almost filled with the pressure sensor 11. On the other hand, the internal space 34S located on the distal side of the internal space 34S, i.e., on a distal side of the pressure sensor 11, is present as the space. The through-holes 34*a* of the housing 34 are opened in the distal side portion of the internal space 34S.

As illustrated in FIG. 3 to FIG. 6, the pressure sensor 11 is provided with a sensor body 12, a diaphragm 13, a bridge circuit 14, four conductive wires 15, and a coating member 16.

Figure 4:
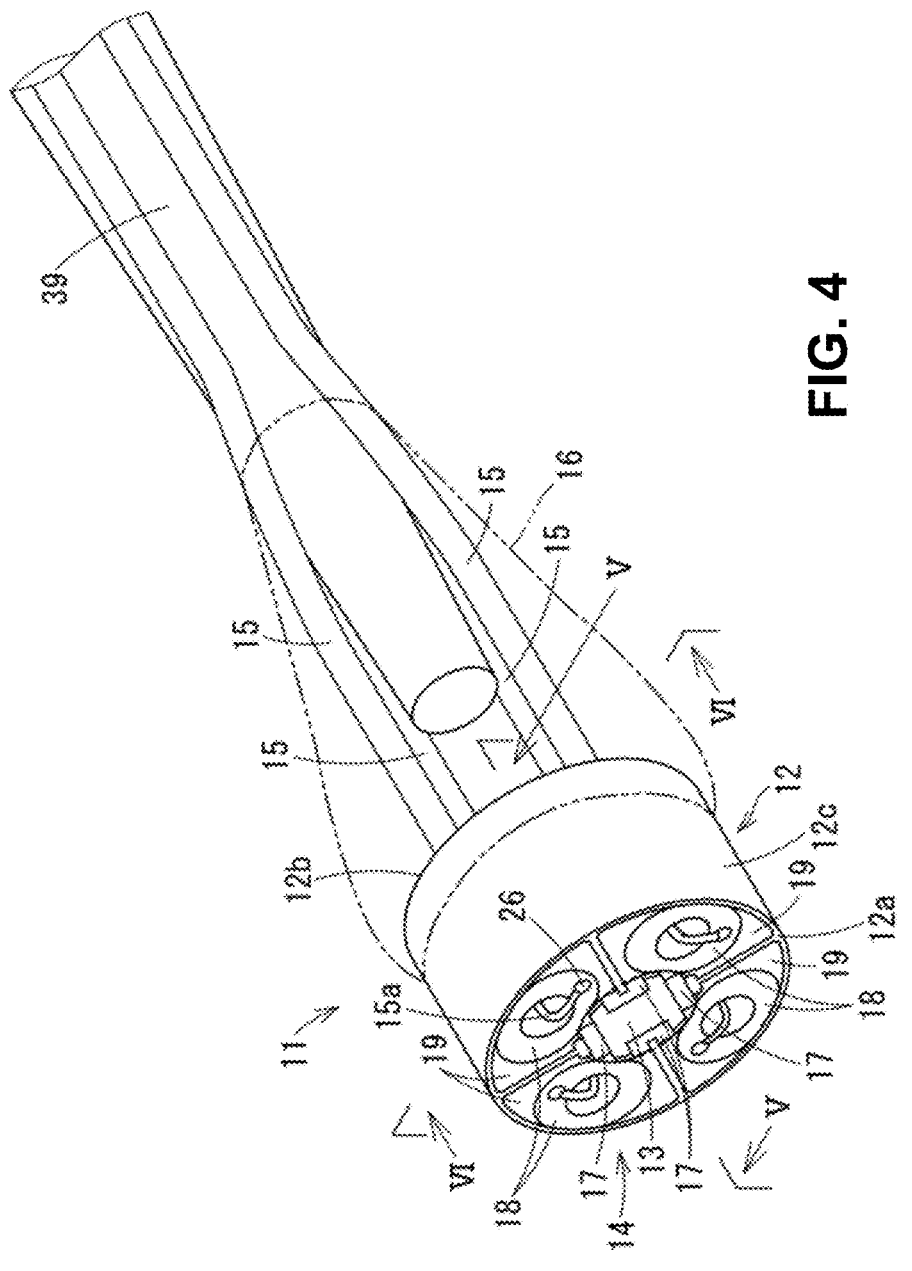
FIG. 4 is a perspective view of a pressure sensor.

As illustrated in FIG. 4, the shape of the sensor body 12 is a cylindrical shape. To the sensor body 12, the diaphragm 13, the bridge circuit 14, and the four conductive wires 15 are attached. The axial center line of the sensor body 12 is parallel to the axial center line 30L. The sensor body 12 has a distal end surface 12*a* facing the distal side, a proximal end surface 12*b* facing the proximal side, and an outer peripheral surface 12*c* facing the radial direction 30R.

Figure 5:
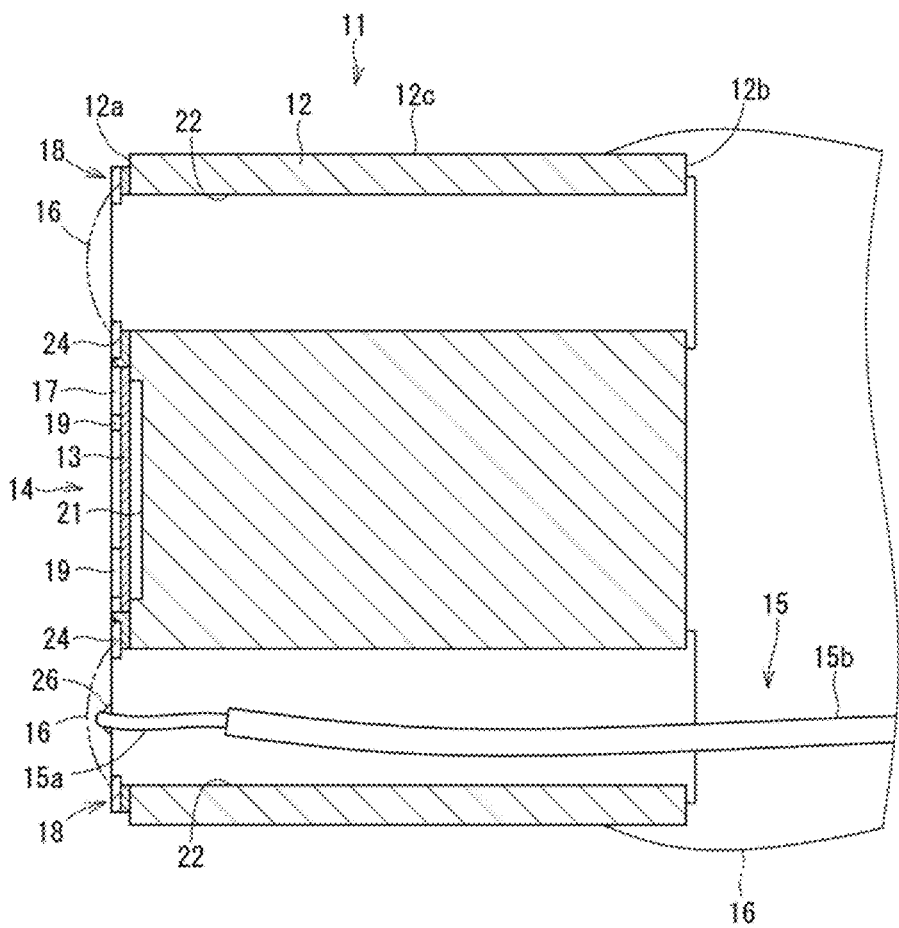
FIG. 5 illustrates cross-sectional views along the cut line V-V of FIG. 4.

As illustrated in FIG. 5, the sensor body 12 has a recessed portion 21. The recessed portion 21 is provided in the sensor body 12 so as to enable the diaphragm 13 to be easily deformed by the pressure of a fluid in a lumen. The recessed portion 21 is opened to the distal end surface 12*a*. The shape of the recessed portion 21 is a circular shape as viewed from the distal side of the sensor body 12. The depth of the recessed portion 21 in the axial direction 30A is constant. The axial center line of the recessed portion 21 is in agreement with the axial center line of the sensor body 12.

Figure 6:
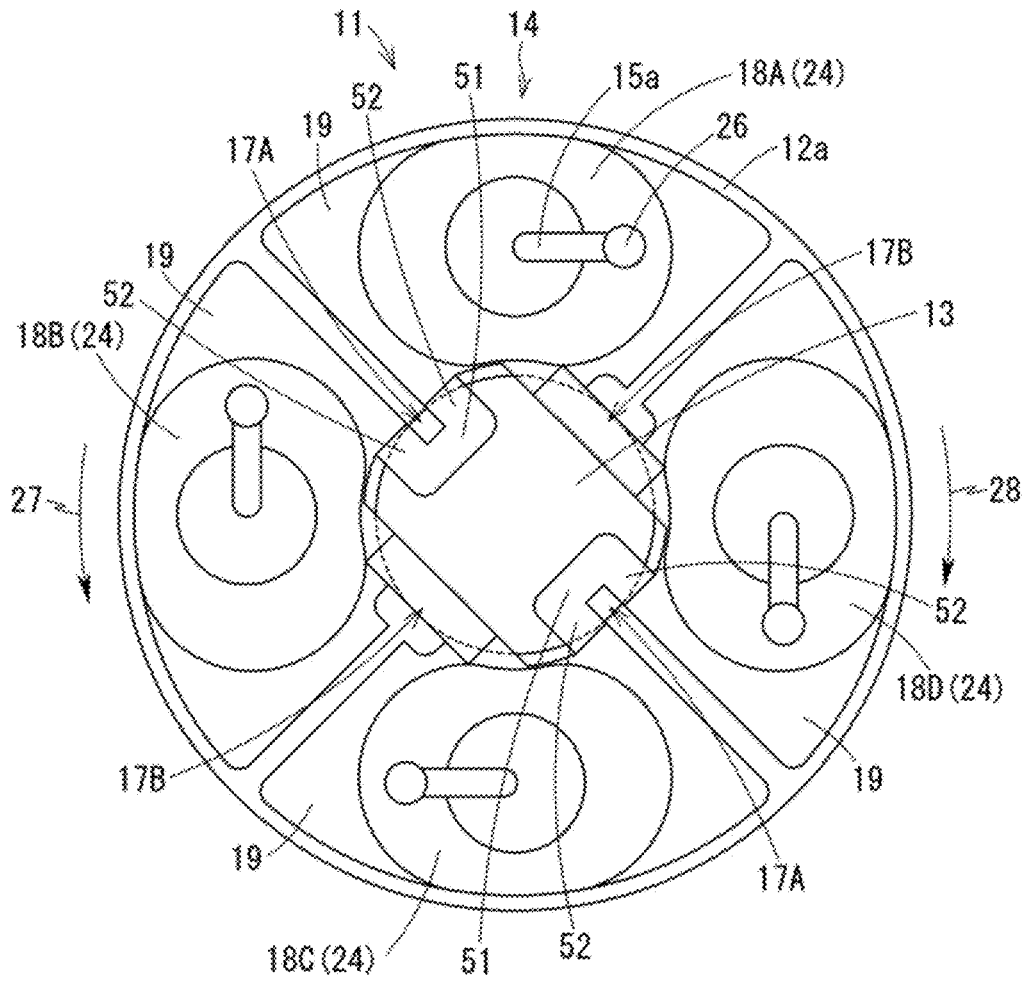
FIG. 6 is a view as viewed from a direction indicated by the arrow VI of FIG. 4.

As illustrated in FIG. 4 to FIG. 6, the sensor body 12 has four through-holes 22. The four through-holes 22 are formed in the sensor body 12 in order to provide four terminals 18 described later in the sensor body 12. The four through-holes 22 are disposed along the circumferential direction 30C at 90° intervals around the axial center line of the sensor body 12. Each through-hole 22 extends along the axial direction 30A and is opened to both the distal end surface 12a and the proximal end surface 12b of the sensor body 12. The shape of the through-hole 22 is a circular shape as viewed from the axial direction 30A.

As illustrated in FIG. 4 to FIG. 6, the diaphragm 13 is disposed on and fixed onto the distal end surface 12a of the sensor body 12. The shape of the diaphragm 13 is a disk shape. More specifically, the shape of the diaphragm 13 is a circular shape as viewed from the axial direction 30A and is a rectangular shape as viewed from the radial direction 30R. The axial center line of the diaphragm 13 and the axial center line of the sensor body 12 are in agreement with each other. The distal end surface 12a, the diaphragm 13, and the recessed portion 21 are coaxially disposed. The outer diameter of the diaphragm 13 is larger than the diameter of the inner peripheral surface of the recessed portion 21. The diaphragm 13 covers the entire opening of the recessed portion 21.

Figure 7:
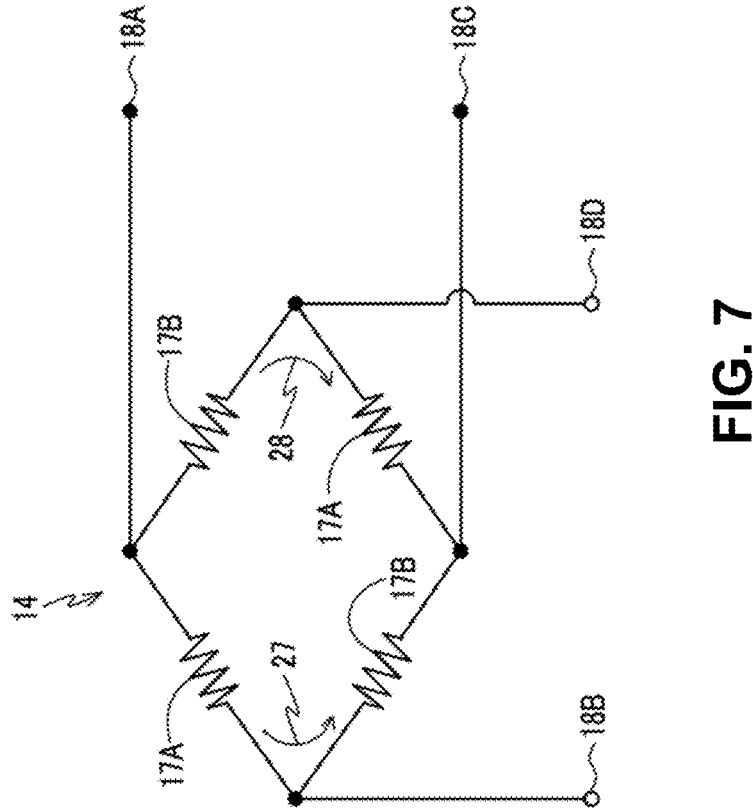
FIG. 7 is a circuit view of a bridge circuit according to the first embodiment of the present invention.

As illustrated in FIG. 4, FIG. 6, and FIG. 7, the bridge circuit 14 is provided with four resistors 17 (17(A), 17B), four terminals 18 (18A, 18B, 18C, 18D), and four connection bodies 19. The bridge circuit 14 surrounds the diaphragm 13.

The bridge circuit 14 is a full bridge circuit in which the four resistors 17 all function as a distortion gauge for measurement. Therefore, the four resistors 17 contain two kinds of resistors different in the resistance variation characteristic. The two kinds of resistors are a first resistor 17A and a second resistor 17B. In this specification, when the first resistors 17A and the second resistors 17B do not need to be distinguished from each other, the first resistors 17A and the second resistors 17B are referred to as the resistors 17.

The four resistors 17 are fixed to the surface on the distal side of the diaphragm 13. The four resistors 17 are fixed to an outer peripheral portion of the diaphragm 13 as viewed from the axial direction 30A. The four resistors 17 are disposed along the circumferential direction 30C at 90° intervals around the axial center line of the sensor body 12. Herein, the first resistors 17A and the second resistors 17B are alternately arranged along the circumferential direction 30C.

Both the first resistors 17A and the second resistors 17B are semiconductors utilizing a piezoelectric resistance effect. The resistors 17 are fixed to the diaphragm 13, and therefore elastically deformed with the elastic deformation of the diaphragm 13. When the resistor 17 is elastically deformed, electrical resistance values of the resistor 17 vary.

The shapes of the first resistors 17A and the second resistors 17B are different from each other. The attitudes of the first resistors 17A and the second resistors 17B to the diaphragm 13 are also different from each other. Due to the differences in the shape and the attitude, the difference in the resistance variation characteristic described above is brought about between the first resistor 17A and the second resistor 17B.

The shape of the first resistor 17A is a square U-shape as viewed from the axial direction 30A. The first resistor 17A is provided with a circumferential direction component 51 and two radial direction components 52 in the attitude to the diaphragm 13. The circumferential direction component 51 extends substantially along the circumferential direction of the diaphragm 13. The radial direction components 52 extend substantially along the radial direction of the diaphragm 13. The first resistors 17A are configured so that the electrical resistance value increases with the deformation of the diaphragm 13 in pressurization.

The shape of the second resistor 17B is a rectangular shape as viewed from the axial direction 30A. The second resistor 17B is configured by a circumferential direction component extending substantially along the circumferential direction of the diaphragm 13 in the attitude to the diaphragm 13. The second resistor 17B is configured so that the electrical resistance value decreases with the deformation of the diaphragm 13 in pressurization.

As illustrated in FIG. 6 and FIG. 7, the four terminals 18 are two input terminals 18A and 18C and two output terminals 18B and 18D in the bridge circuit 14. In this specification, when the input terminals 18A and 18C and the two output terminals 18B and 18D do not need to be distinguished from each other, the input terminals 18A and 18C and the two output terminals 18B and 18D are referred to as the terminals 18. As illustrated in FIG. 5, the four terminals 18 are four electroconductive layers individually provided corresponding to the four through-holes 22 of the sensor body 12. The electroconductive layer contains a distal electroconductive layer 24 laminated around an opening of each through-hole 22 in the distal end surface 12a.

As illustrated in FIG. 4 and FIG. 6, the four terminals 18 are disposed on the outside of the diaphragm 13 in the radial direction 30R. The four terminals 18 are disposed along the circumferential direction 30C at 90° intervals around the axial center line of the sensor body 12. The four terminals 18 and the four resistors 17 are alternately arranged in the circumferential direction 30C. Each terminal 18 is disposed between the two adjacent resistors 17 among the four resistors 17.

As illustrated in FIG. 4 to FIG. 6, the four connection bodies 19 are individually provided corresponding to the four terminals 18. Each connection body 19 is the electroconductive layer laminated around the opening of each through-hole 22 in the distal end surface 12a. Each connection body 19 electrically connects the two adjacent resistors 17 and the terminal 18 located between the two adjacent resistors 17. Thus, the four resistors 17 and the four terminals 18 are alternately electrically connected.

As illustrated in FIG. 6, in the bridge circuit 14, the two input terminals 18A and 18C are disposed at a 180° interval from each other and the two output terminals 18B and 18D are disposed at a 180° interval from each other. As illustrated in FIG. 6 and FIG. 7, the bridge circuit 14 has two paths, one path 27 and the other path 28, from one input terminal 18A toward the other input terminal 18C. The one path 27 is a path passing through the first resistor 17A, one output terminal 18B, and the second resistor 17B. The other path 28 is a path passing through the second resistor 17B, the other output terminal 18D, and the first resistor 17A. Herein, the one input terminal 18A is a high-pressure side and the other input terminal 18C is a low-pressure side.

In a state where a voltage is applied between the two input terminals 18A and 18C, a voltage drop occurs in order of the first resistor 17A and the second resistor 17B in the one path 27 and a voltage drop occurs in order of the second resistor 17B and the first resistor 17A in the other path 28.

In a state where the diaphragm 13 is not pressurized, the first resistors 17A and the second resistors 17B are not deformed. At this time, the electrical resistance values of the first resistor 17A and the second resistor 17B are the same. Therefore, a potential difference is not generated between the two output terminals 18B and 18D.

On the other hand, in a state where the diaphragm 13 is pressurized, the first resistors 17A and the second resistors 17B are deformed. As described above, the electrical resistance value of the first resistors 17A increases and the electrical resistance value of the second resistors 17B decreases in pressurization. More specifically, the voltage drop amount in the first resistors 17A is larger than the voltage drop amount in the second resistors 17B. Therefore, a potential difference is generated between the two output terminals 18B and 18D.

In a state where the guide wire 30 is inserted into a blood vessel, so that blood pressure is applied to the pressure sensor 11, a potential difference is generated between the two output terminals 18B and 18D according to the blood pressure. The magnitude of the blood pressure can be specified based on the potential difference.

As illustrated in FIG. 5, the four conductive wires 15 are individually electrically connected to the four terminals 18. The terminal 18 has the distal electroconductive layer 24 laminated on the distal end surface 12a as described above. To the distal electroconductive layer 24, the conductive wire 15 is connected. The conductive wire 15 has a conductive wire body 15a containing a conductor and an insulation cover 15b containing an insulator. The insulation cover 15b covers the conductive wire body 15a except both end portions of the conductive wire body 15a. In a distal end portion of the conductive wire 15, the conductive wire body 15a is electrically and mechanically connected to the distal electroconductive layer 24 by soldering. By the solder, the connection portion 26 is formed between the conductive wire body 15a and the distal electroconductive layer 24.

As illustrated in FIG. 3 to FIG. 5, the coating member 16 is provided on the proximal side of the sensor body 12. The coating member 16 contains an adhesive in the first embodiment. The coating member 16 is fixed to the proximal end surface 12b of the sensor body 12 and projects from the proximal end surface 12b to the proximal side. The coating member 16 partially proceeds into the four through-holes 22 of the sensor body 12 to close the openings of the four through-holes 22 in the proximal end surface 12b. Distal side end portions of the four conductive wires 15 and the four connection portions 26 are covered with the coating member 16 and fixed to the coating member 16. Herein, the entire conductive wire bodies 15a exposed from the insulation covers 15b are covered with the coating member 16.

As illustrated in FIG. 4 and FIG. 6, the four conductive wire bodies 15a and the four connection portions 26 are covered with the coating member 16 and fixed to the coating member 16 but the coating member 16 is omitted in FIG. 4 and FIG. 6 for explanation. The configuration of the coating member 16 is not limited to an adhesive and may be a solder, a solder paste, or the like.

As illustrated in FIG. 4, the tapered pin 39 is connected to the coating member 16 and fixed to the tapered pin 39. Thus, the sensor body 12 is fixed to the tapered pin 39.

<Calculation Control Portion 40>

As illustrated in FIG. 1, the calculation control portion 40 has the four conductive wires 15 electrically connected to the pressure sensor 11, a power supply portion 41 supplying a current to the pressure sensor 11, a calculation portion 42 performs calculation processing of electric information to be output from the pressure sensor 11, and a connector 43 connected to the four conductive wires 15.

As illustrated in FIG. 1, the power supply portion 41 is configured so as to apply a voltage to the bridge circuit 14 of the pressure sensor 11 through the two conductive wires 15 connected to the two input terminals 18A and 18C.

The calculation portion 42 acquires a voltage value to be output from the bridge circuit 14 of the pressure sensor 11 through the two conductive wires 15 connected to the two output terminals 18B and 18D. The calculation portion 42 calculates the blood pressure acting on the pressure sensor 11 based on a variation in the acquired output voltage value. The calculation portion 42 is provided with a memory 42a. More specifically, the calculation portion 42 calculates the blood pressure as follows.

The memory 42a stores the correspondence relationship between the output voltage value and the blood pressure as described above as data in one to one correspondence, for example. Therefore, when the output voltage value is acquired, the calculation portion 42 can specify the blood pressure corresponding to the output voltage value based on the correspondence relationship stored in the memory 42a. Thus, the calculation portion 42 can calculate the blood pressure acting on the pressure sensor 11 based on the voltage value to be output from the pressure sensor 11.

<Use Example of Pressure Measurement Device 10>

The pressure measurement device 10 is used in order to measure the blood pressure in coronary arteries, for example. The guide wire 30 is inserted into the coronary arteries with the distal end where the tip guide portion 32 is provided as the head in the insertion direction into a blood vessel. The position of the guide wire 30 in the coronary arteries is grasped based on the position of the tip guide portion 32 projected on an X-ray fluoroscopic image of the blood vessel.

When the pressure sensor 11 reaches the measurement position of the blood pressure in the coronary arteries, the insertion of the guide wire 30 is interrupted. In such a state, a fixed voltage is supplied to the pressure sensor 11 from the power supply portion 41 by an operation of a user.

In the blood vessel, blood flows into the internal space 34S of the housing 34, and the blood pressure acts on the surface of the diaphragm 13 of the pressure sensor 11. Thus, the diaphragm 13 is elastically deformed, and then the electrical resistance values of the four resistors 17 accordingly vary.

In the blood flow, pulsation occurs in which an increase and a decrease of the blood pressure are repeated by the motion of the heart. The four resistors 17 are elastically deformed following the pulsation of the blood flow. Thus, the electrical resistance values of the four resistors 17 vary corresponding to the pulsing blood pressure of the blood flow.

The calculation portion 42 of the calculation control portion 40 acquires the electric information to be output from the pressure sensor 11. The calculation portion 42 calculates the blood pressure acting on the pressure sensor 11 based on the electric information as described above.

Operational Effects of First Embodiment

According to the pressure measurement device 10 of the first embodiment, the four resistors 17 are fixed to the outer peripheral portion of the diaphragm 13. Therefore, when the diaphragm is elastically deformed by the pressure (blood pressure) of a fluid in a lumen (blood vessel), the electrical resistance values of the four resistors 17 individually vary. Therefore, the gain of the sensor 11 increases.

The shape of the diaphragm 13 is a disk shape, and therefore, when the diaphragm 13 is elastically deformed, the deformation amount of the outer peripheral portion of the diaphragm 13 is uniform irrespective of the position in the circumferential direction. The variation amount of the electrical resistance values of the resistors 17 is proportional to the deformation amount of the diaphragm 13 at the positions where the resistors 17 are fixed. Therefore, even when the positions of the resistors 17 to the diaphragm 13 somewhat shift due to variations in manufacturing and the like, for example, the resistance variation characteristic of the resistors 17, i.e., the variation amount of the electrical resistance value to the pressure, does not sharply fluctuate. The resistance variation characteristic is kept uniform in the four resistors 17, and therefore a fluctuation of the gain of the sensor 11 due to variations in manufacturing is small.

Each terminal 18 is disposed between the two adjacent resistors 17, and therefore the path length of the bridge circuit 14 is shortened as compared with a case where each terminal 18 is disposed at a position deviated from the position between the two resistors 17. Thus, the size reduction in the sensor 11 is achieved.

Each of the conductive wires 15 is connected to a portion (distal electroconductive layer 24) laminated on the distal end surface 12a of the sensor body 12. Therefore, the conductive wires 15 are not disposed on the outer peripheral surface 12c of the sensor body 12.

A fluid in a lumen does not contact the connection portion 26, and therefore a degradation of the connection portion 26 is suppressed and the connection portion 26 is waterproofed and insulated.

The vibration caused by the contact between the distal end portion (tip guide portion 32) of the guide wire 30 and the wall surface in a lumen is difficult to be transmitted to the sensor 11, and therefore the detection accuracy of the sensor 11 increases.

Modification of First Embodiment

As described above, although the embodiment of the present invention is described in detail, the description above is merely exemplary of the present invention in all points. It is a matter of course that various improvements or modifications can be performed without deviating from the scope of the present invention. With respect to the constituent components of the pressure measurement device 10 according to the first embodiment, constituent components may be omitted, replaced, and added as appropriate according to embodiments. Moreover, the shapes and the sizes of the constituent components of the pressure measurement device 10 may also be set as appropriate according to embodiments. For example, the following alternations can be performed.

In the first embodiment, the shape of the sensor body 12 is a cylindrical shape and the distal end surface 12a is vertical to the axial direction 30A of the guide wire 30. The sensor body 12 may have the distal end surface 12a facing the distal side and the shape of the sensor body 12 and the angle of the distal end surface 12a with respect to the axial direction 30A are not limited. The shape of the sensor body 12 may be a square columnar shape, for example, and the distal end surface 12a may be inclined with respect to the axial direction 30A.

In the first embodiment, the shape of the diaphragm 13 is a disk shape. The shape of the diaphragm 13 is not limited insofar as the shape allows the diaphragm 13 to be elastically deformed according to a variation in the pressure applied to the diaphragm 13. The diaphragm 13 may be a plate-like member and the shape when the plate-like member is viewed from the axial direction 30A may be an arbitrary shape. The arbitrary shape is a polygonal shape and includes a square shape, a hexagonal shape, an octagonal shape, and the like, for example.

In the first embodiment, the coating member 16 contains an adhesive but the present invention is not limited thereto. The coating member 16 may be a rigid component and may be a component to be fixed to the proximal end surface 12b of the sensor body 12, for example.

In the first embodiment, the coating member 16 not only covers the connection portion 26 but fixes the pressure sensor 11 to the tapered pin 39. The coating member 16 may only cover the connection portion 26. In this case, the pressure sensor 11 is fixed to the tapered pin 39 by another member.

In the first embodiment, the four resistors 17 are disposed at 90° intervals around the axial center line of the sensor body 12. The arrangement of the four resistors 17 is not limited insofar as the four resistors 17 are disposed along the circumferential direction 30C in the outer peripheral portion of the diaphragm 13. The four resistors 17 may be disposed around the axial center line of the sensor body 12 at uneven intervals, such as intervals of 120°, 60°, 120°, and 60° or intervals of 60°, 90°, 30°, and 180°, for example.

In the first embodiment, the four through-holes 22 for providing the four terminals 18 are disposed at 90° intervals around the axial center line of the sensor body 12. The arrangement of the four through-holes 22 is not limited insofar as each through-hole 22 is disposed between the two adjacent resistors 17 along the circumferential direction 30C. The four through-holes 22 may be disposed around the axial center line of the sensor body 12 at uneven intervals, such as intervals of 120°, 60°, 120°, and 60° or intervals of 60°, 90°, 30°, and 180°, as with the four resistors 17. Moreover, in the first embodiment, the shape of the through-holes 22 as viewed from the axial direction 30A is a circular shape. The shape of the through-holes 22 as viewed from the axial direction 30A may be a polygonal shape, for example, and is not limited.

In the first embodiment, it is desirable that waterproofing and insulation coating is performed to the entire or a part of the outer surface of the body of sensor 12 to such an extent that the movement of the diaphragm 13 of the sensor body 12 is not hindered. In particular, Parylene (Registered Trademark) coating is desirable but the coating method is not particularly limited.

Second Embodiment

<Guide Wire System 110>

Figure 8:
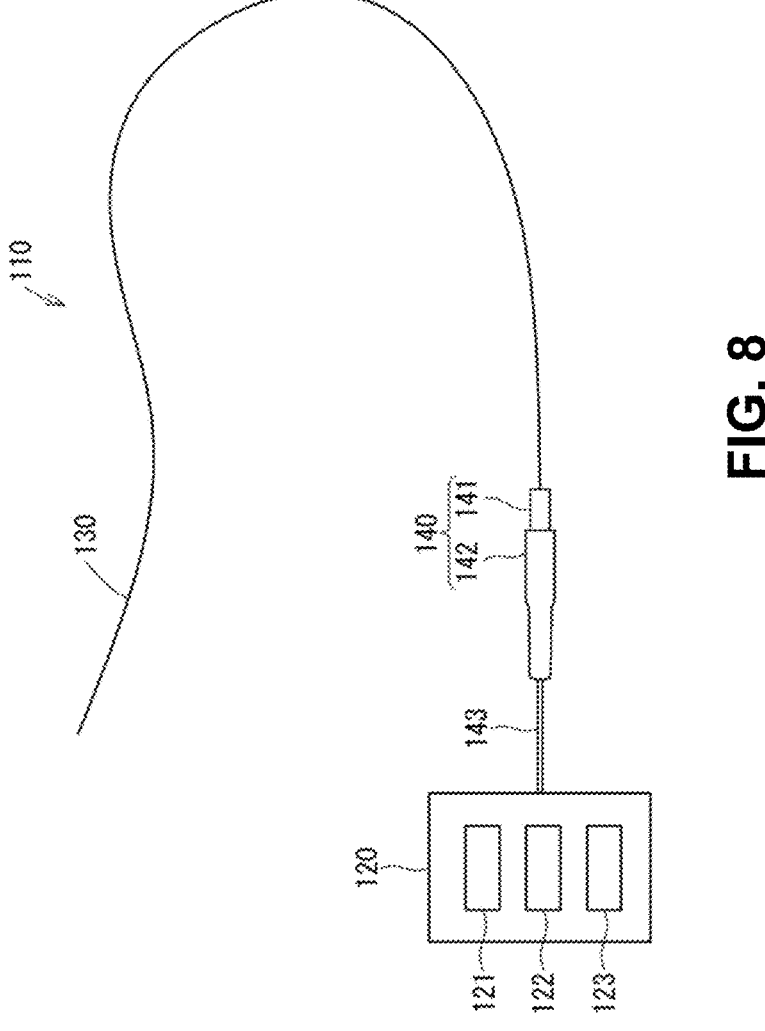
FIG. 8 is a schematic view of a guide wire system according to a second embodiment of the present invention.

As illustrated in FIG. 8, a guide wire system. 110 according to a second embodiment is provided with a guide wire 130, a calculation device 120, and a connector 140 connecting the guide wire 130 and the calculation device 120. The guide wire 130 is a long and narrow cable and can be inserted into blood vessels, such as coronary arteries. The guide wire 130 is provided with a pressure sensor 111 (FIG. 10) outputting electric information according to the pressure in a blood vessel.

The calculation device 120 is provided with a power supply portion 121 supplying a current to the pressure sensor 111 of the guide wire 130, a calculation portion 122 performing calculation processing of the electric information to be output from the pressure sensor 111, and a memory 123 storing information required for the calculation processing. The electric information to be output from the pressure sensor 111 is transmitted to the calculation portion 122 from the guide wire 130 via the connector 140. The calculation portion 122 calculates the blood pressure based on the electric information to be output from the pressure sensor 111. More specifically, the guide wire system 110 is used for the blood pressure measurement.

In FIG. 8, a fixed end (end connected to the calculation control device 120) is a proximal end (lower left end in FIG. 8) of both ends of the guide wire 30 and a free end (tip when inserted into a blood vessel) thereof is a distal end (upper left end in FIG. 8). Hereinafter, in the guide wire 130, the side where the proximal end is present is referred to as a proximal side and the side where the distal end is present is referred to as a distal side.

<Guide Wire 130>

Figure 9:
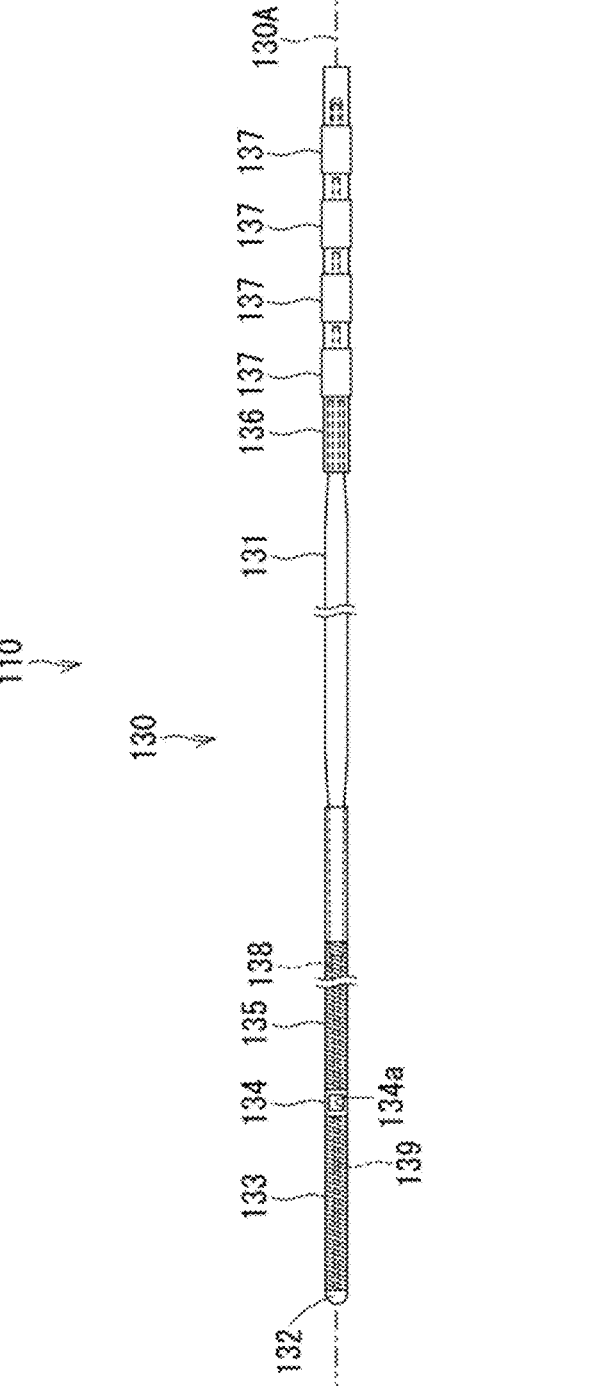
FIG. 9 is a view illustrating a guide wire according to the second embodiment of the present invention.

FIG. 9 illustrates the guide wire 130. In FIG. 9, the left side is the distal side of the guide wire 130 and the right side is the proximal side of the guide wire 130. The guide wire 130 is provided with a tip guide portion 132, a first spiral body 133, a housing 134, a second spiral body 135, an electrode pipe 136, four contacts 137, a tapered pin 138, and a tip guide pin 139. A core wire 131 extends from the proximal end to the distal side. The tip guide portion 132 is disposed at the distal end. The first spiral body 133, the housing 134, the second spiral body 135, and the electrode pipe 136 are disposed in order toward the proximal end from the tip guide portion 132 at the distal end. The four contacts 137 are disposed on the outer periphery side of the electrode pipe 136 and are arranged along an axis line 130A of the guide wire 130. The axis line 130A refers to the axis line of the guide wire 130 when the guide wire 130 is in a straight state without being deflected or curved.

Figure 18:
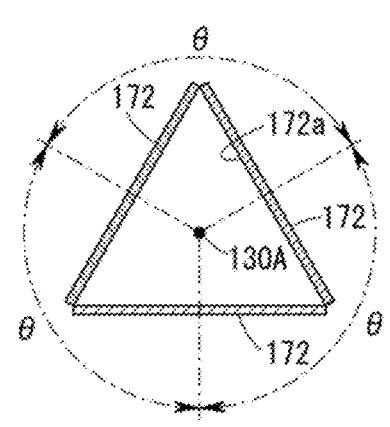
FIGS. 18(A), 18(B), and 18(C) are cross-sectional view along the cut line XI-XI of FIG. 16 and particularly
Figure 18:
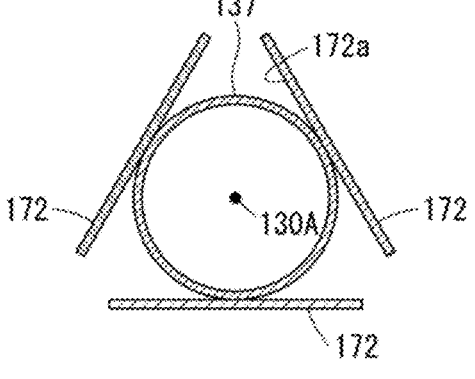
Figure 18:
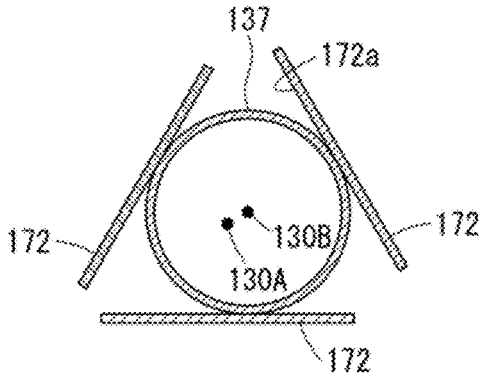

The core wire 131 is a member configuring the skeleton of the guide wire 130. The tip guide portion 132 is a hemispherical member which is disposed at the distal end and protrudes to the distal side and which abuts on a blood vessel wall to thereby guide the movement direction of the guide wire 130 along the blood vessel. The first spiral body 133 and the second spiral body 135 are spirally wound wire rods and configured so as to be easier to bend than the core wire 131 so that a distal end portion of the guide wire 130 is easy to conform to a blood vessel. The housing 134 is a casing accommodating the pressure sensor 111 in the internal space. The housing 134 has two through-holes 134a. Blood can contact the pressure sensor 111 (FIG. 10) disposed inside the housing 134 through the through-holes 134a. The electrode pipe 136 is a cylindrical member accommodating four conductive wires 115 (FIG. 10) extending from the pressure sensor 111 and is fixed to a proximal end portion of the core wire 131. The four contacts 137 are individually connected to the four conductive wires 115 (FIG. 10) and fixed to the outer peripheral surface of the electrode pipe 136. The shape of the contact 137 is an annular shape (FIGS. 18(A)-18(C)). The tapered pin 138 is a member reinforcing the bending rigidity of the second spiral body 135, fixed to a distal end portion of the core wire 131, and extends from the core wire 131 to the housing 134. The tip guide pin 139 is a member reinforcing the bending rigidity of the first spiral body 133 and is fixed to the housing 134 and the tip guide portion 132.

Figure 10:
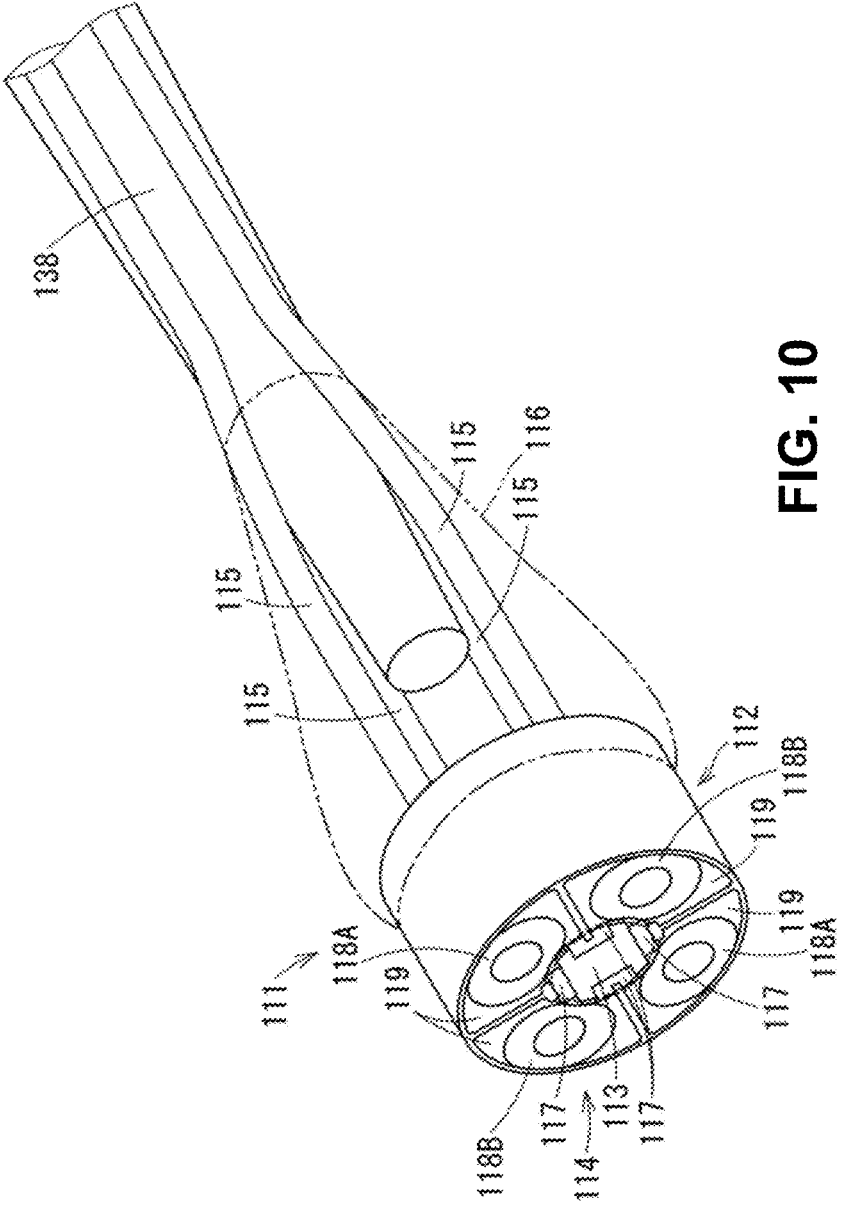
FIG. 10 is a perspective view of a pressure sensor.

As illustrated in FIG. 10, the pressure sensor 111 is provided with a sensor body 112, a diaphragm 113, a bridge circuit 114, four conductive wires 115, and a connection portion 116, for example. The sensor body 112 is fixed to a tapered pin 138 fixed to the core wire 131 by the connection portion 116 containing an adhesive, for example. To the sensor body 112, the diaphragm 113, the bridge circuit 114, and the four conductive wires 115 are attached. The bridge circuit 114 is a full bridge circuit in which four resistors 117 all function as a distortion gauge for measurement. The bridge circuit 114 is provided with the four resistors 117, four terminals 118A and 118B, and four connection bodies 119. The four resistors 117 are fixed to the diaphragm 113. The four terminals 118A and 118B contain two input terminals 118A and two output terminals 118B. Each connection body 119 electrically connects each of the resistors 117 to each of the terminals 118A and 118B. Each of the conductive wires 115 is electrically connected to each of the terminals 118A and 118B.

In a state where the guide wire 130 is inserted into a blood vessel, so that blood pressure is applied to the pressure sensor 111, the diaphragm 113 is elastically deformed according to the blood pressure. The four resistors 117 are elastically deformed with the elastic deformation of the diaphragm 113, so that the electrical resistance values of the four resistors 117 vary. When a voltage is applied between the two input terminals 118A in this state, a potential difference is generated between the two output terminals 118B. Based on the potential difference, the magnitude of the blood pressure can be specified in the calculation device 120 (FIG. 8).

<Connector 140>

Figure 11:
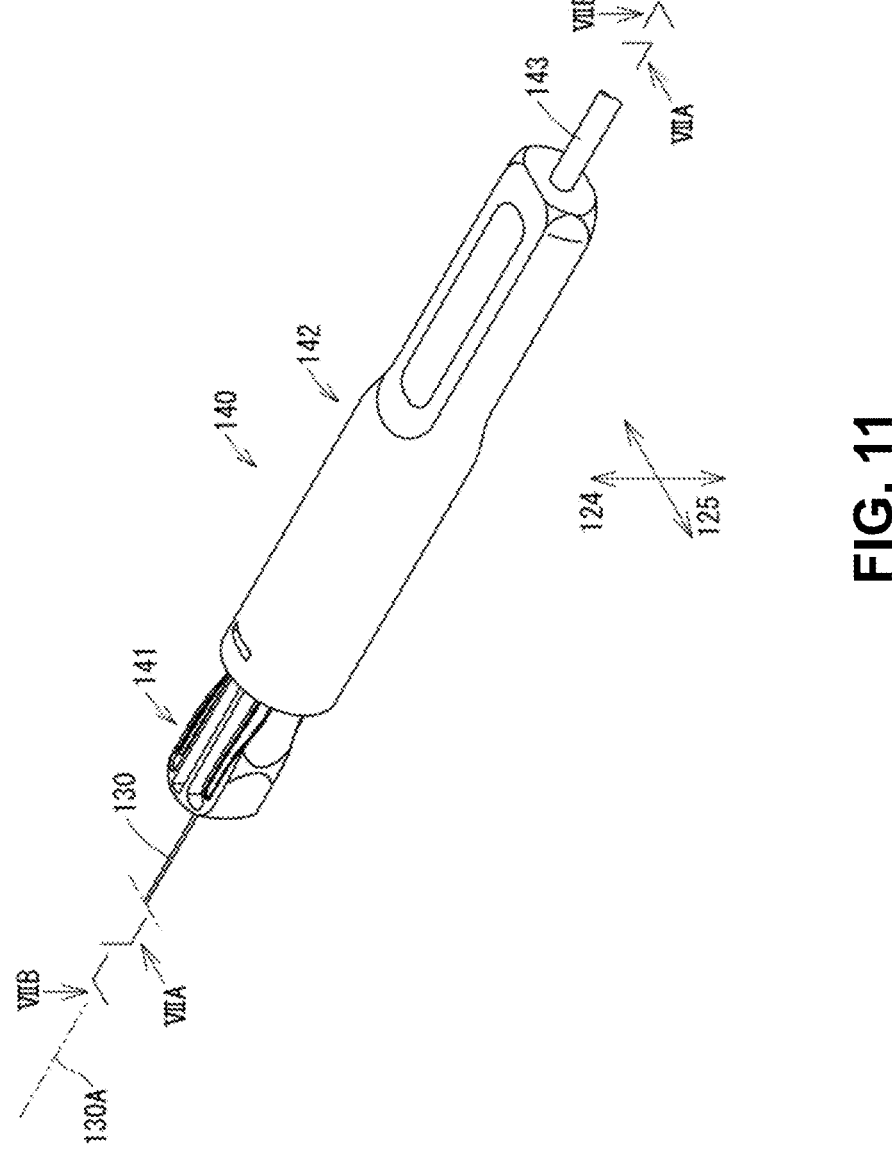
FIG. 11 is a perspective view of a connector according to the second embodiment of the present invention.

As illustrated in FIG. 11, the connector 140 is provided with a holding component (example of the holding portion) 141 holding the guide wire 130 and a connector body 142 to which the holding component 141 is attached. The connector body 142 is provided with a cable 143 electrically connected to the four conductive wires 115. The cable 143 is electrically connected to the calculation device 120 (FIG. 8).

Figure 13:
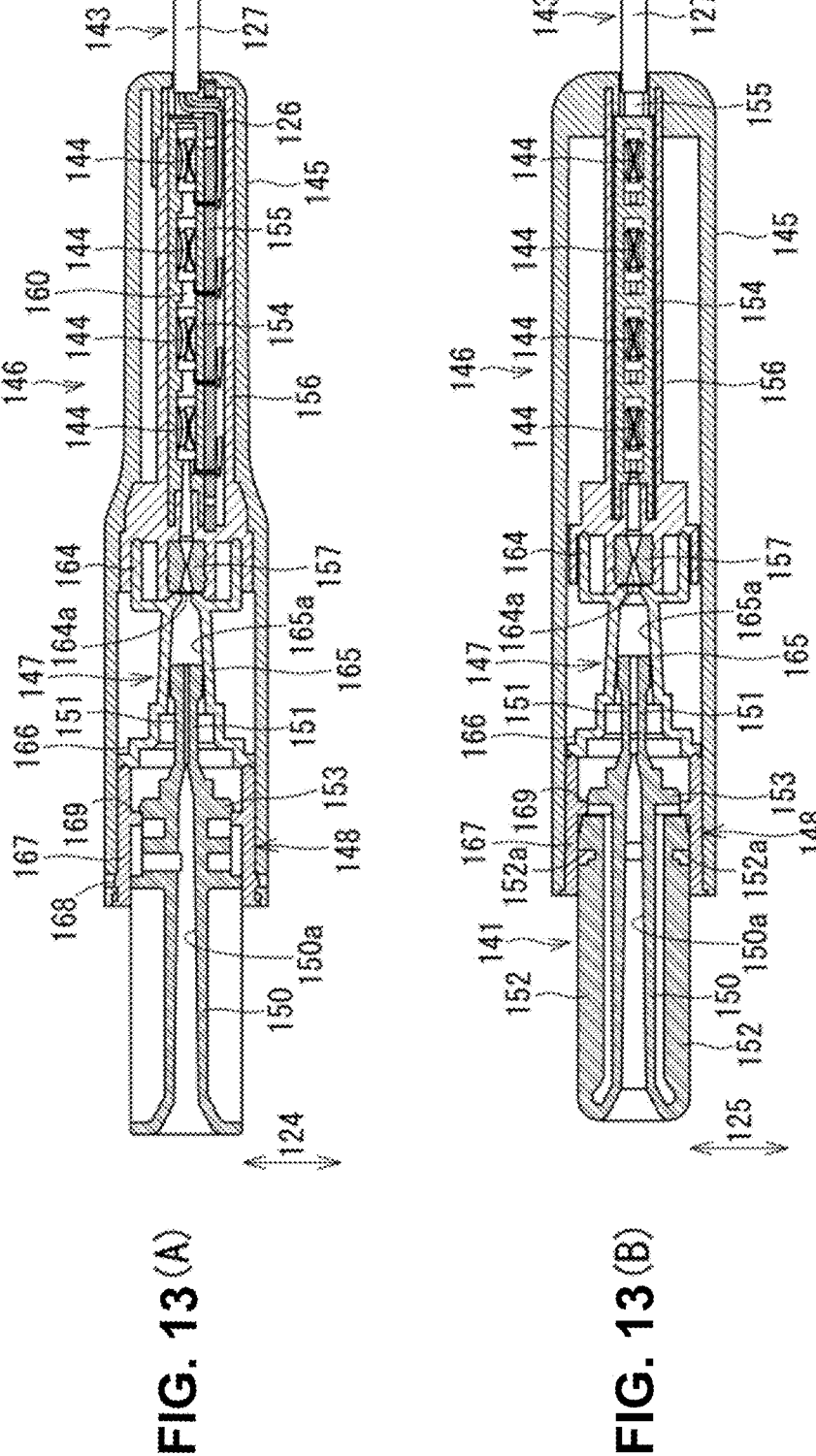
FIGS. 13(A) and 13(B) are cross-sectional views of the connector according to the second embodiment of the present invention in a non-lock state and particularly
Figure 14:
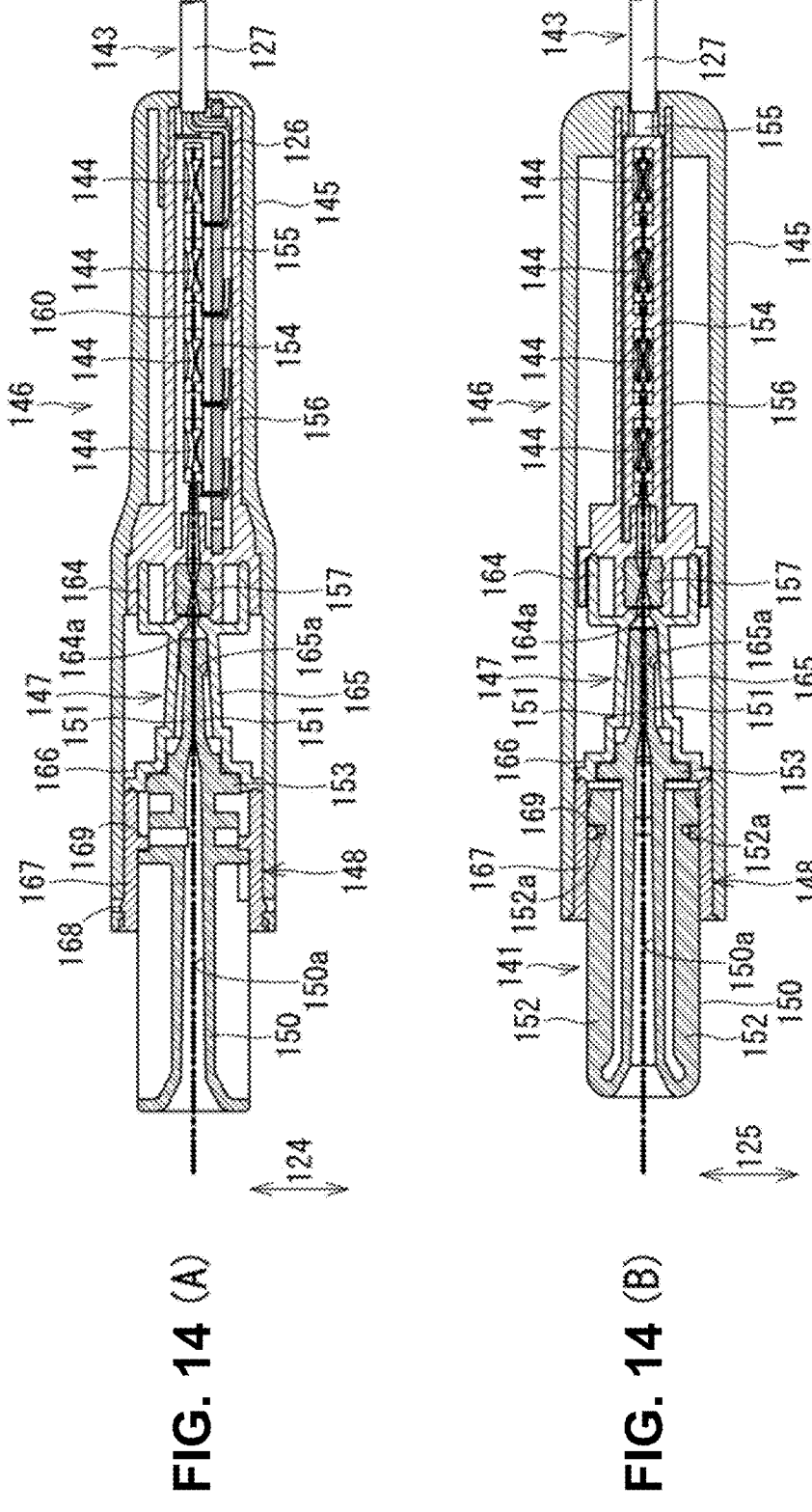
FIGS. 14(A) and 14(B) are cross-sectional views of the connector according to the second embodiment of the present invention in a lock state and particularly

In FIG. 11, a first direction 124 and a second direction 125 are directions orthogonal to the axis line 130A. The first direction 124 and the second direction 125 are orthogonal to each other. Hereinafter, the attitude of the connector 140 is described using the first direction 124 and the second direction 125. FIG. 13(A) and FIG. 14(A) are cross-sectional views cut by the plane including the axis line 130A and in parallel to the first direction 124. FIG. 13(B) and FIG. 14(B) are cross-sectional views cut by the plane including the axis line 130A and in parallel to the second direction 125.

Figure 12:
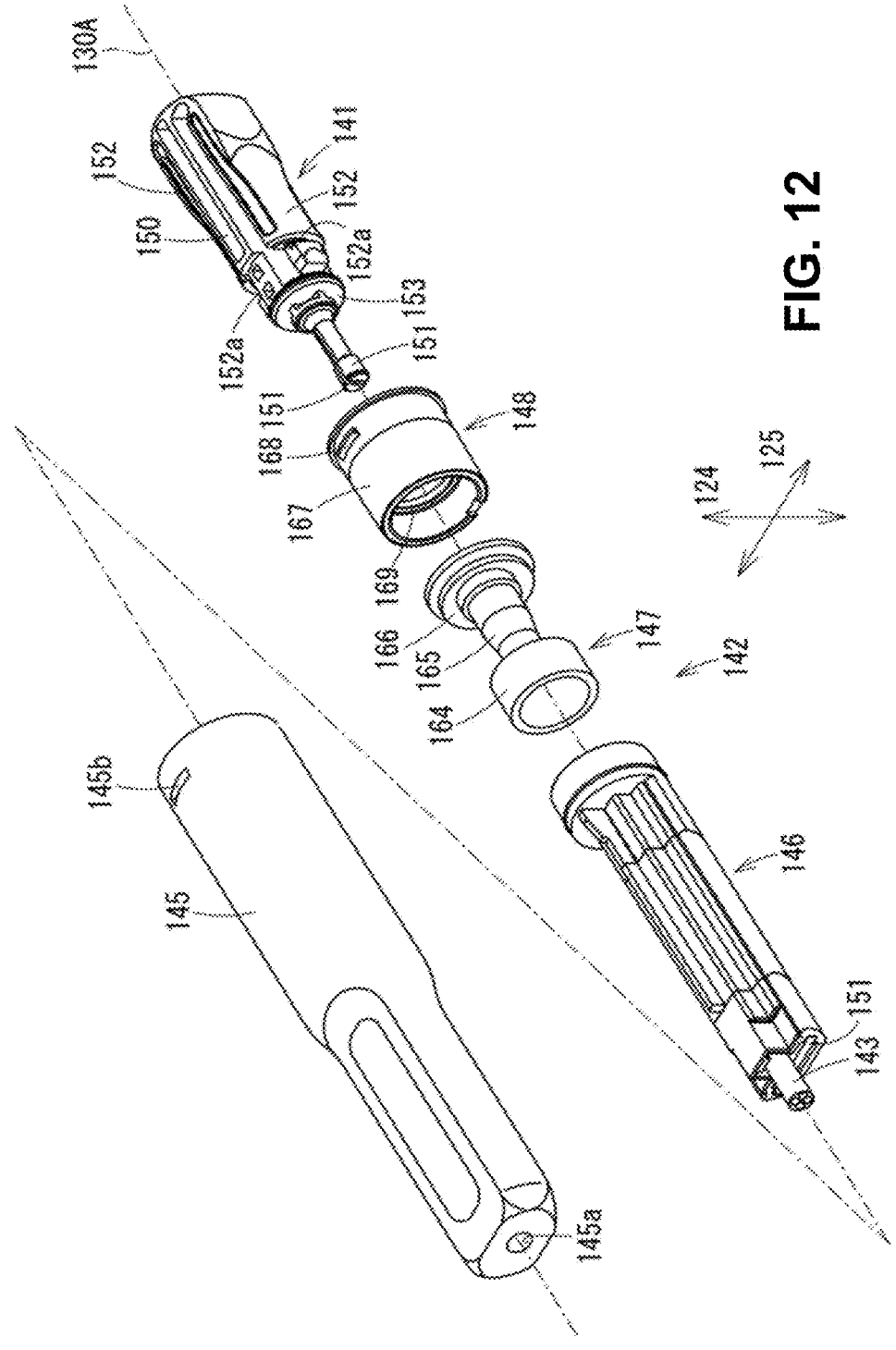
FIG. 12 is an exploded perspective view of the connector according to the second embodiment of the present invention.

FIG. 12 is an exploded perspective view of the connector 140. The connector body 142 is provided with a tubular cover 145, a terminal case 146, a guide component (example of the guide portion) 147, and a support component (example of the support portion) 148.

The holding component 141 is illustrated in FIG. 12 to FIGS. 14(A)-14(B). As illustrated in FIG. 12, the holding component 141 is provided with a body 150, two holding pieces 151, and two hook portions 152. The holding component 141 is molded by a resin material. Therefore, the body 150, the two holding pieces 151, and the two hook portions 152 are integrally molded.

The shape of the body 150 is schematically a tubular shape in which an insertion hole 150a which is the internal space extends along the axis line 130A. The guide wire 130 can be inserted into and passed through the insertion hole 150a. The body 150 is provided with a fitting portion 153 in a proximal end portion. The shape of the fitting portion 153 is a disk shape with the axis line 130A as the axis and projects outward in the radial direction. The fitting portion 153 is fitted to the guide component 147 by being combined with the connector body 142 as the holding component 141 and regulates the movement of the holding component 141 in a direction of being inserted into the connector body 142. Moreover, the fitting portion 153 abuts on a lock portion 169 of the support component 148 to thereby prevent the holding component 141 which is inserted into the connector body 142 once from easily falling off from the connector body 142.

The two holding pieces 151 extend along the axis line 130A from the proximal end (left side of FIG. 12, right side of FIGS. 13(A)-13(B)) of the body 150. The two holding pieces 151 face each other in the second direction 125. The shape of each of the two holding pieces 151 is a semicylindrical shape extending along the axis line 130A. When the two holding pieces 151 approach each other to abut on each other, a substantially cylindrical shape is formed. The two holding pieces 151 are apart from each other in the second direction 125 in a state where no external force is given. In the holding pieces 151, the proximal end sides can be elastically deformed in a direction of approaching each other with the connection position between each of the holding pieces 151 and the body 150, i.e., distal end of each of the holding pieces 151, as a fulcrum. The guide wire 130 is inserted into and passed through the holding component 141 through space serving as the internal space when the two holding pieces 151 form the cylindrical shape. Due to the fact that a proximal end portion of each of the holding pieces 151 abuts on the guide component 147, the two holding pieces 151 are elastically deformed so as to approach each other. Thus, the guide wire 130 is held by the two holding pieces 151.

The two hook portions 152 extend along the axis line 130A toward the proximal side (left side of FIG. 12, right side of FIGS. 13(A)-13(B)) from the distal end (left side of FIG. 12, right side of FIGS. 13(A)-13(B)) of the body 150. In the second direction 125, the body 150 is located between the two hook portions 152. In the hook portions 152, the proximal end sides can be elastically deformed inward in the radial direction with respect to the axis line 130A with the connection position between each of the hook portions 152 and the body 150, i.e., distal end of each of the hook portions 152, as a fulcrum. Recessed portions 152a are formed in a proximal end portion of each of the hook portions 152. Each recessed portion 152a is recessed inward in the radial direction with respect to the axis line 130A in each of the hook portions 152. Each recessed portion 152a can be engaged with the lock portion 169 of the support component 148. Due to the fact that each recessed portion 152a is engaged with the lock portion 169 of the support component 148, the relative movement of the holding component 141 along the axis line 130A with respect to the connector body 142 is regulated.

The tubular cover 145 is illustrated in FIG. 12 to FIGS. 14(A)-14(B). The tubular cover 145 accommodates the terminal case 146 accommodating terminals 144, the guide component 147, and the support component 148 which are disposed in order from the proximal side (lower left side of FIG. 12) toward the distal side (upper right side of FIG. 12). The terminal case 146, the guide component 147, and the support component 148 accommodated in the tubular cover 145 are assembled to each other to be integrated.

The shape of the tubular cover 145 is schematically a tubular shape extending along the axis line 130A. The outer shape of the proximal end side of the tubular cover 145 is a rectangular tubular shape. The proximal end of the tubular cover 145 is sealed and a cable hole 145a penetrated along the axis line 130A is formed. The cable 143 is extended from the inside of the tubular cover 145 to the outside through the cable holes 145a. The distal end side of the tubular cover 145 has a cylindrical shape. Around the distal end of the peripheral wall of the tubular cover 145, two engagement holes 145b penetrated in the radial direction with respect to the axis line 130A are formed. The two engagement holes 145b face each other in the first direction 124. A convex portion 168 of the support component 148 is engaged with each engagement hole 145b. The distal end of the tubular cover 145 is opened.

Figure 15:
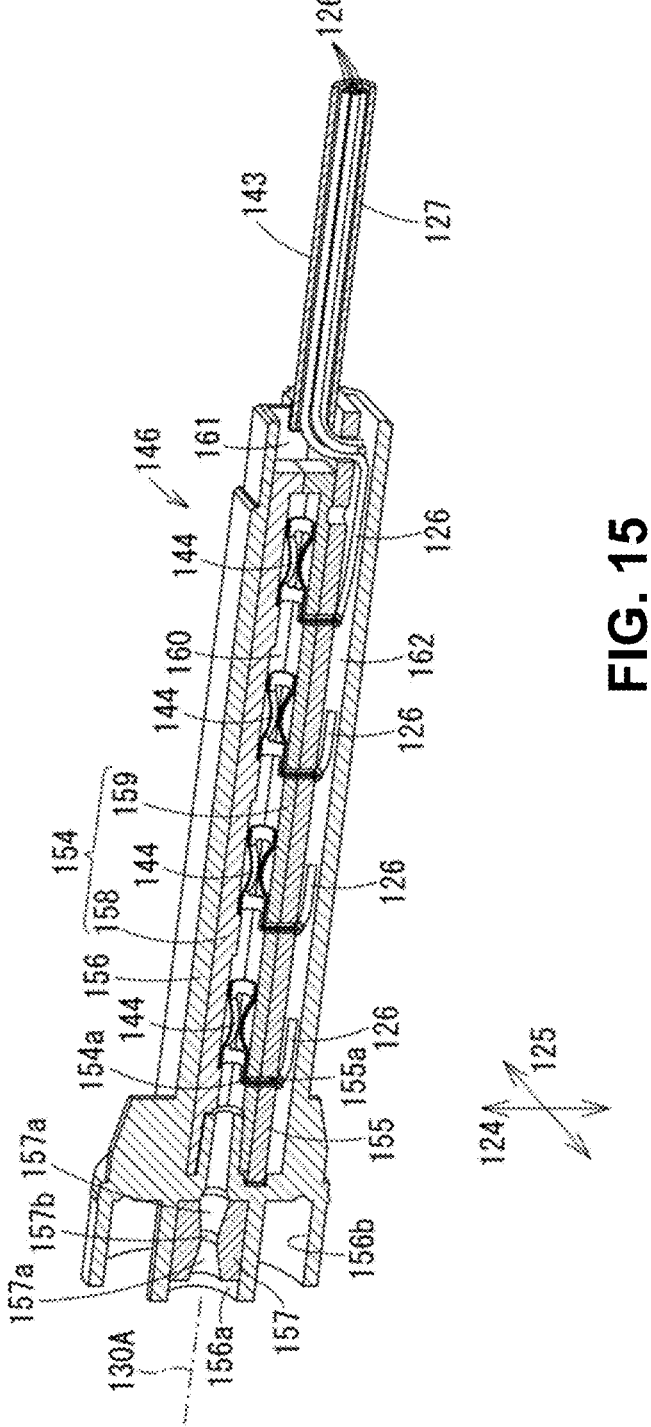
FIG. 15 is a cross-sectional perspective view of a terminal case according to the second embodiment of the present invention along the cut line VIA-VIA of FIG. 11.

As illustrated in FIG. 12 to FIG. 15, the terminal case 146 is provided with the four terminals 144 (FIGS. 13(A)-13(B) to 18A-18D) individually electrically connected to the four contacts 137 of the guide wire 130. As illustrated in FIG. 15, the terminal case 146 is provided with an inner case 154 accommodating the four terminals 144, a connection plate 155 to which the cable 143 is fixed, an outer case 156 accommodating the inner case 154 and the connection plate 155, and a wire guide component 157.

As illustrated in FIG. 15, the cable 143 has four conductive wires 126 and a protective coating film 127 covering the four conductive wires 126. The four conductive wires 126 are individually electrically connected to the four terminals 144 in the terminal case 146.

The inner case 154 is a long and narrow rectangular parallelepiped configured by combining a first case piece 158 and a second case piece 159. The first case piece 158 and the second case piece 159 face each other in the first direction 124 and long and narrowly extends along the axis line 130A. Between the first case piece 158 and the second case piece 159, space 160 extending along the axis line 130A is formed. In the space 160, the four terminals 144 are arranged side by side along the axis line 130A. The distal end of the inner case 154 is opened and the space 160 is continuous to the outside through the opening.

The connection plate 155 is a plate facing the first case piece 158 and the second case piece 159 in the first direction 124. The second case piece 159 is adjacent to the connection plate 155. In the second case piece 159, four terminal holes 154a are formed along the first direction 124. In the connection plate 155, four terminals holes 151a are provided along the first direction 124. Each terminal hole 151a of the connection plate 155 is continuous to each terminal hole 154a of the second case piece 159. A connection portion 170 of the terminal 144 is inserted into and passed through one pair of the terminal hole 154a and the terminal hole 151a.

Between the connection plate 155 and the outer case 156, spaces 161 and 162 along the axis line 130A are formed on both sides in the first direction 124. In the space 161, the inner case 154 and a distal end portion of the protective coating film 127 of the cable 143 are disposed. In the space 162, the four connection portions 170 of the four terminals 144 project, the four conductive wires 126 of the cable 143 are disposed, and each of the connection portions 170 is electrically connected to each of the conductive wires 126 by soldering. Some conductive wires 126 are illustrated in a broken state for convenience of illustration.

The outer case 156 has a substantially square tubular shape. In a distal end portion of the outer case 156, a first recessed portion 156a and a second recessed portion 156b of a cylindrical shape opened to the distal side are formed. The internal space of the first recessed portion 156a is continuous to the internal space of the inner case 154 accommodated in the outer case 156. The first recessed portion 156a and the second recessed portion 156b each have internal space along the axis line 130A. The wire guide component 157 is fitted to the first recessed portion 156a. A first tube portion 164 of the guide component 147 is fitted to the second recessed portion 156b.

The wire guide component 157 is a component positioning the guide wire 130 inserted into the connector 140 along the axis line 130A. The wire guide component 157 has a through-hole having a cylindrical shape and penetrated along the axis line 130A. The inner surface of the through-hole has two tapered surfaces 157a which are individually disposed on the distal side and the proximal side and the diameter of which individually decreases toward the center and a circumferential surface 157b connecting the two tapered surfaces 157a. The inner diameter of the circumferential surface 157b is somewhat larger than the outer diameter of the guide wire 130. The minimum diameter of the tapered surface 157a is equal to the inner diameter of the circumferential surface 157b and the maximum diameter of the tapered surfaces 157a is larger than the inner diameter of the circumferential surface 157b. Each tapered surface 157a is tapered toward the circumferential surface 157b. Therefore, the guide wire 130 inserted into the wire guide component 157 is guided so as to be coaxial with the axis line 130A by the circumferential surface 157b.

The guide component 147 is illustrated in FIG. 12 to FIGS. 14(A)-14(B). The guide component 147 is a component guiding the holding component 141 so that distal portions of the two holding pieces 151 of the holding component 141 are elastically deformed when the holding component 141 is slid along the axis line 130A.

As illustrated in FIG. 12, the guide component 147 is provided with a first tube portion 164, a guide portion 165, and a second tube portion 166 (example of the fitting target portion) disposed in order from the proximal side (lower left side of FIG. 12) toward the distal side (upper right side of FIG. 12). The first tube portion 164, the guide portion 165, and the second tube portion 166 are integrally molded. The shape of the first tube portion 164 is a bottomed cylindrical shape and the first tube portion 164 has a through-hole 164a along the axis line 130A. The guide wire 130 is inserted into and passed through the through-hole 164a. The first tube portion 164 is fitted to the second recessed portion 156b of the terminal case 146 from the outside so as to be rotatable around the axis line 130A. The guide portion 165 is rotatable with respect to the terminal case 146.

As illustrated in FIG. 12, the shape of the guide portion 165 is a tubular shape with a tapered inner surface. As illustrated in FIGS. 13(A)-13(B) and FIGS. 14(A)-14(B), the inner surface of the guide portion 165 is a guide surface 165a formed along the axis line 130A. The guide surface 165a is a tapered surface tapered toward the proximal side (right side of FIGS. 13(A)-13(B) and FIGS. 14(A)-14(B)).

As illustrated in FIG. 12 to FIGS. 14(A)-14(B), the shape of the second tube portion 166 is a schematically cylindrical shape. The inner diameter and the outer diameter of the second tube portion 166 are gradually vary in three steps so that the second tube portion 166 expands toward the distal side along the axis line 130A. To the distal side of the second tube portion 166, the support component 148 is fitted. To the internal space of the second tube portion 166, the fitting portion 153 of the body 150 is fitted The support component 148 is illustrated in FIG. 12 to FIGS. 14(A)-14(B). The support component 148 is a component supporting the holding component 141 rotatably around the axis line 130A. The support component 148 is provided with a body 167, two convex portions 168, and a lock portion 169. The shape of the body 167 is a cylindrical shape having internal space extending along the axis line 130A. Each convex portion 168 projects outward in the radial direction with respect to the axis line 130A from the outer peripheral surface of the body 167. The two convex portions 168 are disposed facing each other in the first direction 124 corresponding to the two engagement holes 145b of the tubular cover 145. The lock portion 169 projects inward in the radial direction with respect to the axis line 130A from the inner peripheral surface of the body 167. The lock portion 169 is a protrusion continuously extending around the axis line 130A. In a state where the recessed portions 152a of the hook portion 152 of the holding component 141 are engaged with the lock portion 169, the movement along the axis line 130A of the holding component 141 is regulated by the lock portion 169 and the holding component 141 is guided by the lock portion 169 to be rotatable around the axis line 130A.

With reference to FIGS. 13(A)-13(B) and FIGS. 14(A)-14(B), the connector 140 in a non-lock state and in a lock state is described. FIGS. 13(A)-13(B) illustrate the connector 140 in the non-lock state. FIGS. 14(A)-14(B) illustrate the connector 140 in the lock state.

The connector body 142 can be disassembled as illustrated in FIG. 12 and the terminal case 146, the guide component 147, and the support component 148 are accommodated in the tubular cover 145 and assembled to each other to be integrated. The holding component 141 is attachable to and detachable from the connector body 142.

When the removed holding component 141 is attached to the connector body 142, the holding component 141 is inserted with the holding pieces 151 as the insertion front side from the distal side (left side of FIGS. 13(A)-13(B)) toward the proximal side (right side of FIGS. 13(A)-13(B)) of the connector body 142. The outer diameter of the fitting portion 153 is somewhat larger than the outer diameter of the lock portion 169. However, the fitting portion 153 is formed of a resin material, and therefore can be elastically deformed. Therefore, external force is applied so that the holding component 141 is pressed into the connector body 142, whereby the fitting portion 153 can move to the proximal side over the lock portion 169. When the fitting portion 153 is located on the proximal side of the lock portion 169, the fitting portion 153 abuts on the lock portion 169, whereby the holding component 141 is prevented from falling off from the connector body 142. Moreover, external force is applied so that the holding component 141 is pulled out from the connector body 142, whereby the fitting portion 153 moves to the distal side over the lock portion 169, so that the holding component 141 is removed from the connector body 142.

When the fitting portion 153 is located on the proximal side of the lock portion 169, the non-lock state and the lock state of the connector 140 can be switched. When the fitting portion 153 is not fitted to the second tube portion 166 of the guide component 147, the connector 140 is in the non-lock state (FIGS. 13(A)-13(B)). When the fitting portion 153 is fitted to the second tube portion 166 of the guide component 147, the connector 140 is in the lock state (FIGS. 14(A)-14(B)). In the non-lock state, the guide wire 130 is not locked to the connector 140. In the non-lock state, the holding pieces 151 are located in the guide portion 165 but do not abut on to the guide surface 165a. The two holding pieces 151 are kept in a separated state, and therefore, even when the guide wire 130 is inserted into the connector 140, the two holding pieces 151 do not hold the guide wire 130.

External force is applied so as to sandwich the two hook portions 152, whereby the two hook portions 152 are elastically deformed to move inward in the radial direction.

Thus, the proximal ends of the hook portions 152 are located inside in the radial direction relative to the lock portion 169, so that the proximal ends of the hook portions 152 can move to the proximal end side of the connector body 142 relative to the lock portion 169. When the holding component 141 further moves to the proximal side, the fitting portion 153 is fitted to the second tube portion 166 to abut on the same, so that the holding component 141 is inhibited from further moving to the proximal side of the connector body 142. In the state where the fitting portion 153 is fitted to the second tube portion 166, the recessed portions 152a of the hook portion 152 face the lock portion 169. When the external force applied to the two hook portions 152 is released, the hook portion 152 which is elastically restored move outward in the radial direction, so that the recessed portions 152a and the lock portion 169 are engaged with each other. As a result, the connector 140 is brought into the lock state illustrated in FIGS. 14(A)-14(B). In the lock state, the holding component 141 cannot relatively move in a direction along the axis line 130A with respect to the connector body 142 but the holding component 141 is rotatable around the axis line 130A with respect to the connector body 142.

The guide wire 130 is inserted into the connector 140 in the non-lock state. The guide wire 130 is inserted from the insertion hole 150a of the holding component 141 through a gap between the two holding pieces 151 and the wire guide component 157 until the proximal end of the guide wire 130 abuts on the inner wall of the proximal end of the inner case 154. At this time, the four contacts 137 of the guide wire 130 individually contact the four terminals 144 in the space 160.

By the movement of the holding component 141 to the proximal side with respect to the connector body 142, the connector 140 is brought into the lock state from the non-lock state. At this time, by the movement of the proximal end portions of the holding pieces 151 to the proximal side while abutting on the guide surface 165a, the proximal end portions of the two holding pieces 151 are elastically deformed so as to mutually move inward in the radial direction. Thus, the guide wire 130 inserted into the connector 140 is held so as to be held between the two holding pieces 151. Thus, the guide wire 130 is held so as not to be pulled out from the connector 140 depending on the external force applied to the guide wire 130 in a usual operation. Moreover, the guide wire 130 rotates integrally with the holding component 141, and therefore, when the holding component 141 relatively rotates around the axis line 130A with respect to the connector body 142, the guide wire 130 also relatively rotates around the axis line 130A with respect to the connector body 142 together with the holding component 141. Herein, the holding pieces 151 abut on the guide surface 165a, and therefore the guide component 147 also rotates together with the holding component 141.

In the connector 140 in the lock state, the two hook portions 152 are moved inward in the radial direction by external force, whereby the recessed portions 152a of the hook portion 152 are separated from the lock portion 169, so that the holding component 141 becomes movable along the axis line 130A. In this state, the holding component 141 is moved to the distal side with respect to the connector body 142, whereby the connector 140 is brought into the non-lock state from the lock state.

<Terminal 144>

The terminal 144 is described with reference to FIG. 16 to FIGS. 18(A)-18(C). As illustrated in FIG. 16 and FIGS. 17(A)-17D, the terminal 144 is provided with the connection portion 170, a first connection portion 171, three terminal portions 172, and a second connection portion 173. The material of the terminal 144 is metal which has conductivity and can be subjected to bending processing and is preferably spring steel. The connection portion 170, the first connection portion 171, the three terminal portions 172, and the second connection portion 173 are integrally formed by performing punching and bending processing of a metal plate.

The connection portion 170 is a portion electrically connected to the conductive wire 126 of the cable 143. The connection portion 170 has a long and narrow flat plate shape bent into an L shape. The first connection portion 171 and the second connection portion 173 individually connect both ends in the axis line 130A of the three terminal portions 172. The first connection portion 171 and the second connection portion 173 each have a substantially cylindrical shape.

The three terminal portions 172 are disposed around the axis line 130A. The terminal portions 172 have the same shape and individually have a long and narrow plate shape along the axis line 130A, and the center in a direction along the axis line 130A is curved so as to swell inward in the radial direction. The angle $\theta$ serving as the pitch (interval) around the axis line 130A in the adjacent terminal portions 172 is 120° (FIG. 18(A)). In other words, the center or one edge of a surface directed in the axis line 130A in each of the terminal portions 172 is individually different in phase by 120°.

Figure 16:
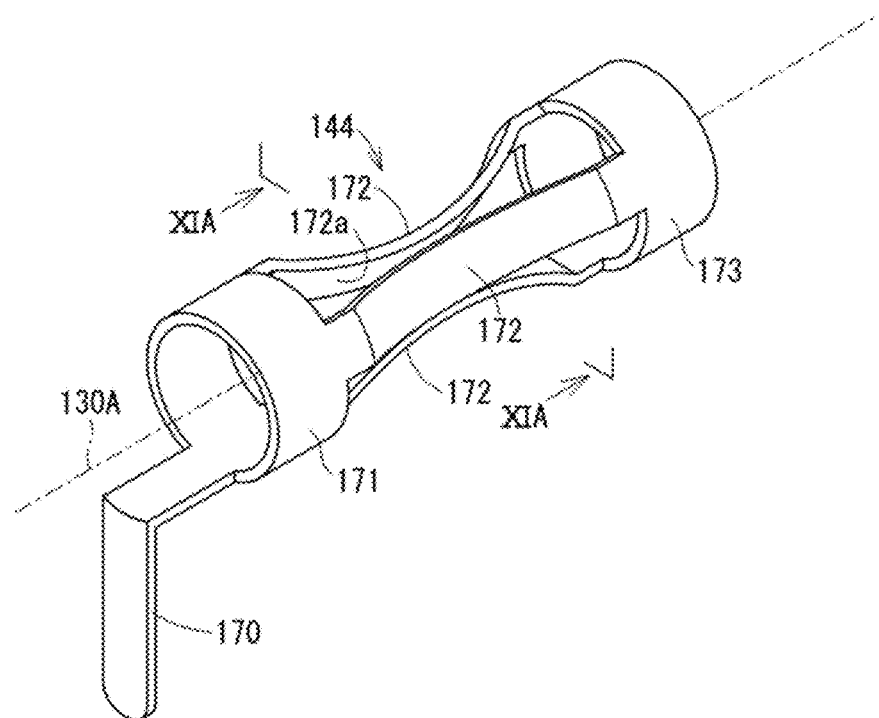
FIG. 16 is a perspective view of a terminal of the connector according to the second embodiment of the present invention.
Figure 17:
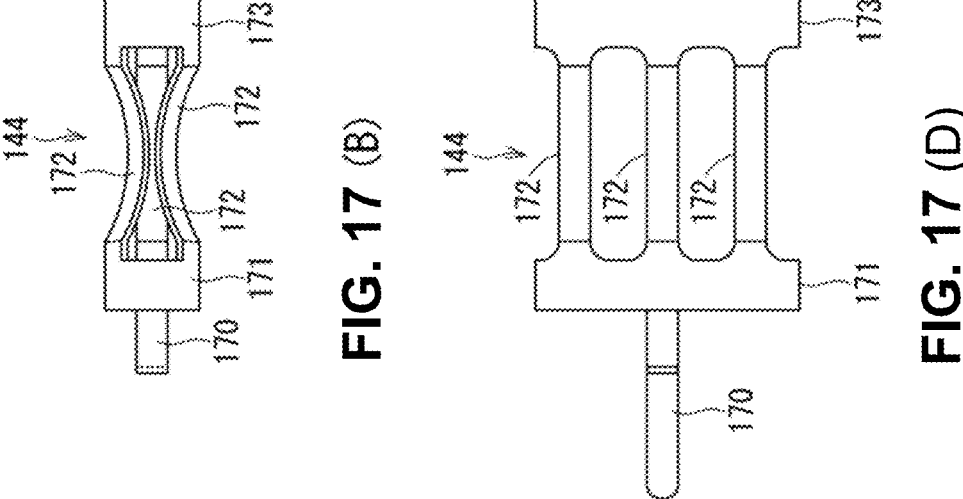
FIGS. 17(A), 17(B), 17(C), and 17(D) are views of the terminal of the connector according to the second embodiment of the present invention and particularly

The inner surface of the terminal portions 172 is a contact surface 172a facing the contact 137 of the guide wire 130. As illustrated in FIG. 16 and FIG. 17(C), the cross section of the contact surface 172a cut along the plane including the axis line 130A is curved so as to protrude inward in the radial direction with respect to the axis line 130A. Moreover, as illustrated in FIG. 16 and FIG. 17(A), the contact surface 172a in the cutting plane orthogonal to the axis line 130A is a straight line. When the guide wire 130 is held by the connector 140, each of the contact surfaces 172a contacts the contact 137 in a portion closest to the axis line 130A. The contact 137 is a circumferential surface, and therefore the contact between the contact surface 172a and the contact 137 is a so-called point contact.

The terminal portions 172 have elasticity as a plate spring by the curved shape. In a state where each of the contacts 137 of the guide wire 130 abuts on each of the terminal portions 172, each of the terminal portions 172 is elastically deformed outward in the radial direction.

Changes in the positions of the three terminal portions 172 are described with reference to FIGS. 18(A)-18(C). Each view of FIGS. 18(A)-18(C) illustrates the cross section of the terminal 144 at the position closest to the axis line 130A in the terminal portions 172.

FIG. 18(A) illustrates the positions of the terminal portions 172 in a natural state, i.e., a state where the contact 137 of the guide wire 130 does not abut on the terminal 144.

FIG. 18(B) illustrates the positions of the terminal portions 172 in a state where the contact 137 of the guide wire 130 abuts on the terminal 144. The radius of the outer peripheral surface of the contact 137 is larger than the shortest distance from the axis line 130A to the contact surfaces 172a of the terminal portions 172. Therefore, each of the terminal portions 172 is elastically deformed outward in the radial direction by abutting on the contact 137. Thus, each of the contact surfaces 172a move outward in the radial direction from the natural state. The axis line of the guide wire 130 in FIG. 18(B) is in agreement with the axis line 130A in the connector 140. Therefore, the contact surface 172a of each of the terminal portions 172 is located at a position apart from the axis line 130A corresponding to a distance equal to the radius of the outer peripheral surface of the contact 137. Each of the terminal portions 172 is elastically deformed, and therefore each of the terminal portions 172 is energized toward the contact 137 by the restoring force. Thus, each of the terminal portions 172 pressure-contacts the contact 137, so that the electrical connection between the terminal 144 and the contact 137 is maintained.

FIG. 18(C) also illustrates the positions of the terminal portions 172 in the state where the contact 137 of the guide wire 130 abuts on the terminal 144. An axis line 130B of the guide wire 130 in FIG. 18(C) is located at a position deviated from the axis line 130A of the connector 140. Such a state occurs by performing an operation of rotating the guide wire 130 or the like by a user. The operation of the guide wire 130 is performed when moving the guide wire 130 forward and backward within a blood vessel, for example. For example, when the guide wire 130 rotates, the holding component 141 holding the guide wire 130 also rotates together. The holding component 141 is rotatably supported by the support component 148. Therefore, the guide wire 130 rotates relatively to the connector body 142 laid on a desk, for example. The rotation of the connector body 142 is suppressed by abutting of an outer shape portion of a rectangular shape of the tubular cover 145 on the placement surface of the desk, for example.

When the guide wire 130 rotates relatively to the connector body 142, the contact 137 of the guide wire 130 rotates relatively to the terminals 144 of the connector 140. The holding component 141 holding the guide wire 130 rotates relatively to the connector body 142, and therefore a tolerance or a backlash is present therebetween. By a rotation torque of the guide wire, the holding component 141 rattles with respect to the connector body 142. As a result, the contact 137 moves in the radial direction, so that the axis line 130B of the guide wire 130 is deviated from the axis line 130A of the connector 140. Thus, even when the contact 137 moves in the radial direction, the three terminal portions 172 follow the movement of the contact 137 by the energization force generated by the elastic deformation of the three terminal portions 172. Therefore, the electrical connection between the three terminal portions 172 and the contact 137 is maintained. In addition thereto, the contact 137 is returned to the position of the axis line 130A by the balance of the energization force of the three terminal portions 172, and therefore the position of the contact 137 is likely to return to the position of FIG. 18(B) from the position of FIG. 18(C).
<Use Example of Guide Wire System 110>

The guide wire system 110 is used for measuring the blood pressure in coronary arteries, for example. The guide wire 130 is inserted into the coronary arteries with the distal end where the tip guide portion 132 is provided as the head in the insertion direction into a blood vessel.

When the pressure sensor 111 reaches the blood pressure measurement position in the coronary arteries, the insertion of the guide wire 130 is interrupted. In such a state, a fixed voltage is supplied to the pressure sensor 111 from the power supply portion 121 by an operation of a user.

In a blood vessel, blood flows into the internal space of the housing 134, so that the blood pressure acts on the surface of the diaphragm 113 of the pressure sensor 111. Thus, the diaphragm 113 is elastically deformed, and accordingly the electrical resistance values of the four resistors 117 vary.

In the blood flow, pulsation occurs in which an increase and a decrease of the blood pressure are repeated by the motion of the heart. The four resistors 117 are elastically deformed following the pulsation of the blood flow. Thus, the electrical resistance values of the four resistors 117 vary corresponding to the pulsing blood pressure of the blood flow.

The calculation portion 122 of the calculation control device 120 acquires the electric information to be output from the pressure sensor 111. The calculation portion 122 calculates the blood pressure acting on the pressure sensor 111 based on the electric information as described above.

When the blood pressure measurement position is changed during the blood pressure measurement, an operation of, for example, rotating or sliding the guide wire 130, is performed as necessary in order to change the position of the guide wire 130. When the guide wire 130 is operated, the contact 137 of the guide wire 130 moves in the radial direction by a rotation torque, for example. Each of the terminal portions 172 of the terminals 144 provided in the connector 140 follows the movement in the radial direction of the contacts 137. Therefore, the electrical connection between the contacts 137 and the terminals 144 is maintained also in the situation where a rotation torque has been applied. Therefore, a jump or a drift is difficult to occur in data to be transmitted to the calculation device 120 from the pressure sensor 111.

Operational Effects of Second Embodiment

According to the connector 140 of the second embodiment, the holding component 141 is slid along the axis line 130A of the insertion hole 150a with respect to the support component 148, whereby the holding pieces 151 abut on the guide surface 165a to be elastically deformed inward in the radial direction. As a result, the guide wire 130 is held by the holding pieces 151. When slid in the opposite direction, the holding pieces 151 are separated from the guide surface 165a, so that the hold of the guide wire 130 is released. Therefore, the guide wire 130 is held or the hold is released by sliding the holding component 141.

Due to the fact that each recessed portion 152a is engaged with the lock portion 169 of the support component 148, the relative movement of the holding component 141 along the axis line 130A with respect to the support component 148 is regulated.

In the case where the holding pieces 151 abut on the guide surface 165a, even in the state where the lock portion 169 is not temporarily engaged with the recessed portions 152a by the elastic deformation of the hook portions 152, the fitting portion 153 is fitted to the second tube portion 166 to abut on the same, so that the movement of the holding component 141 to the proximal side of the support component 148 is inhibited.

The angle θ around the axis line 130A of the guide wire 130 between the two adjacent terminal portions 172 satisfies the relationship of 90°<θ<180°. Therefore, even when the contacts 137 move in the radial direction so that the axis lines 130A and 130B of the guide wire 130 shift, the terminal portions 172 follow the movement of the contacts 137 by the elastic deformation of the terminal portions 172. Therefore, a trouble that the electrical connection between the contacts 137 and the terminals 144 is momentarily cut is difficult to occur.

The angle θ satisfies the relationship θ=120°, and therefore the three terminal portions 172 are disposed at equal intervals. Therefore, even when the guide wire 130 moves in any direction of the radial directions, each of the terminal portions 172 follows the contact 137. Therefore, the trouble that the electrical connection between the contact 137 and the terminal 144 is momentarily cut is more difficult to occur.

The terminal portions 172 point-contact the contacts 137 along the axis line 130A of the guide wire 130. Therefore, when the guide wire 130 moves along the axis line 130A, the terminal portions 172 easily retreat in a direction of separating from the axis line 130A. Accordingly, the guide wire 130 can be easily inserted into and removed from the connector 140.

The lock portion 169 locks the slide at the position where the holding pieces 151 abut on to the guide surface 165a and enables the guide component 147 to rotate around the axis line 130A of the guide wire 130. Therefore, when the connector body 142 is placed on a work desk in the state where the guide wire 130 is held by the holding component 141, the tubular cover 145 itself does not rotate and the guide component 147 and the holding component 141 become rotatable. Accordingly, the connector body 142 itself does not rotate by the vibration in the operation of the guide wire, and therefore the trouble that the electrical connection is momentarily cut is difficult to occur.

<Contact Stability Data>

Figure 21:
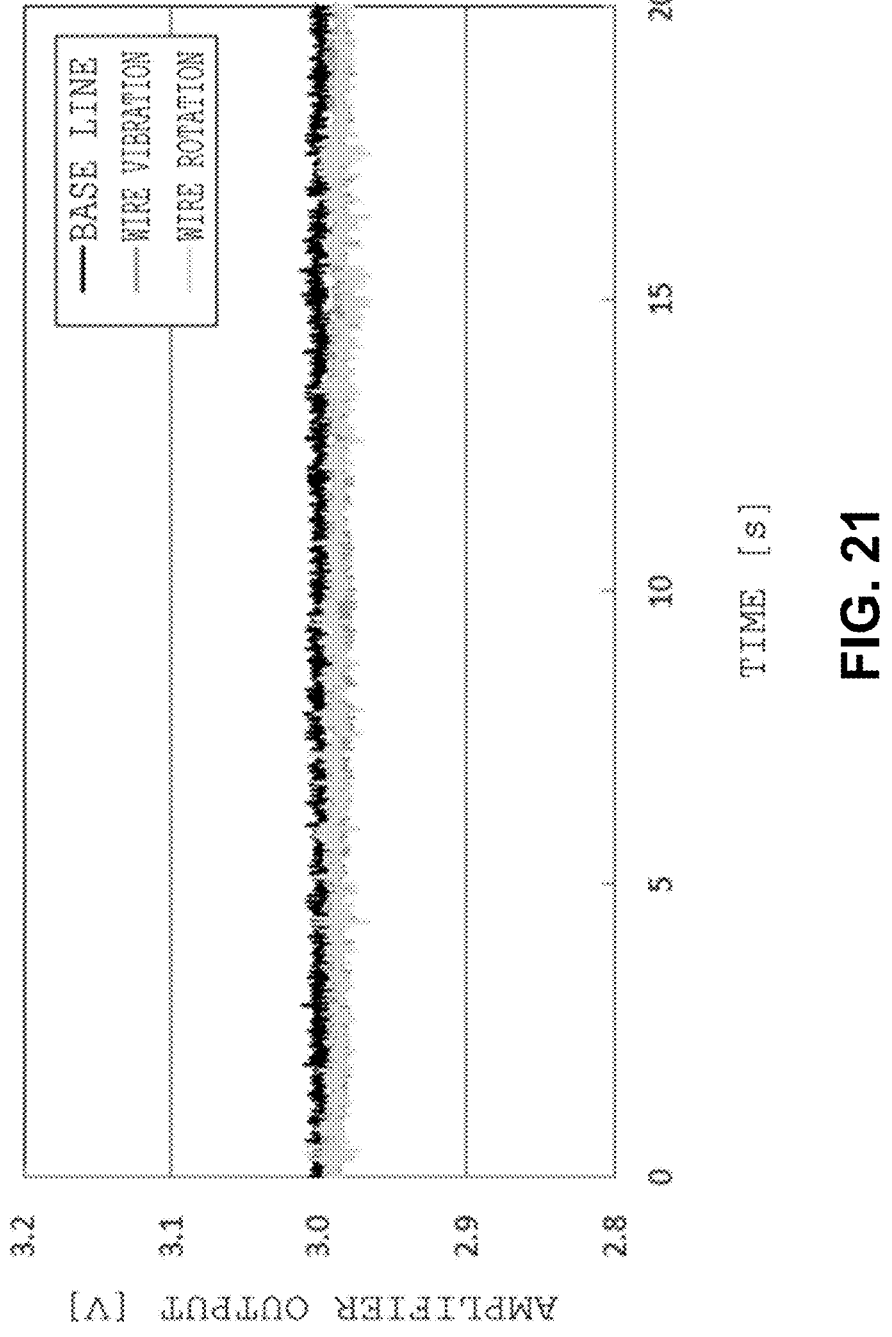
FIG. 21 illustrates contact stability data of Amplifier input (V)–Time (S) according to the second embodiment of the present invention.
Figure 22:
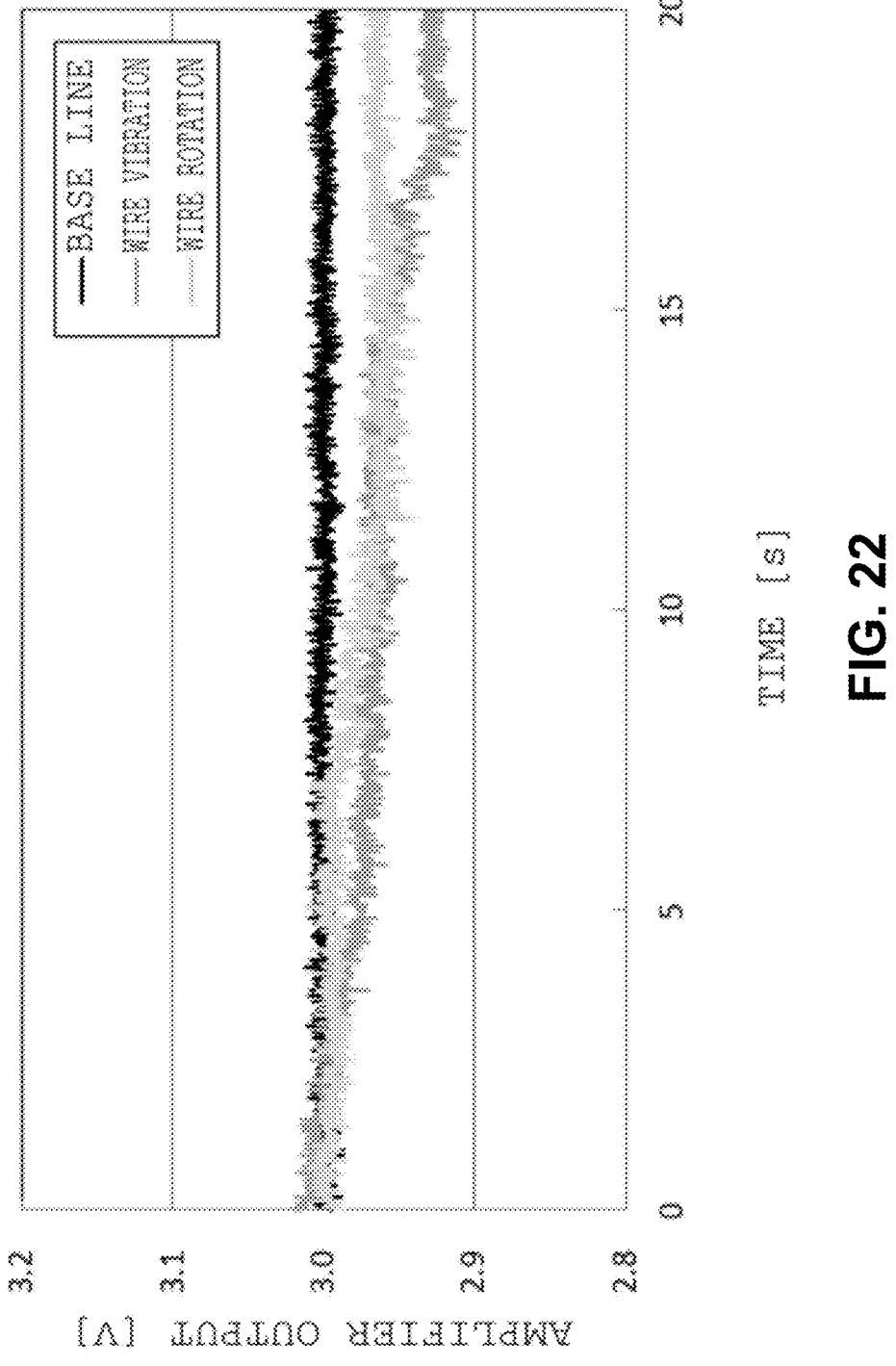
FIG. 22 illustrates contact stability data of Amplifier input (V)–Time (S) about Combowire of Volcano as a comparative article.
Figure 23:
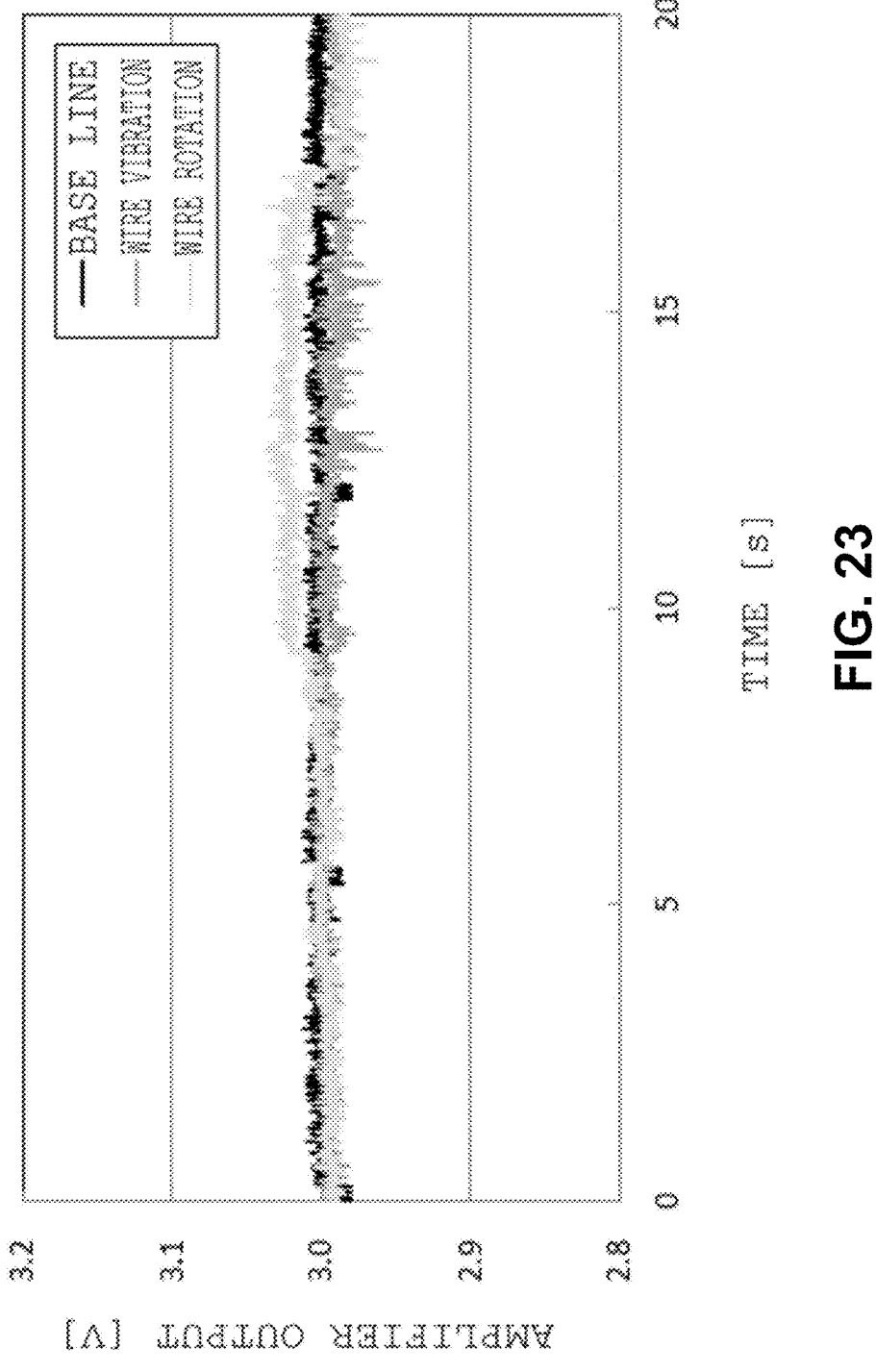
FIG. 23 illustrates contact stability data of Amplifier input (V)–Time (S) about Certus of St Jude Medical as a comparative article.

An experiment method for confirming the contact stability of the terminals 144 and experimental results are described with reference to FIG. 21 to FIG. 23.

An experiment of evaluating the electric contact stability as a female terminal was performed for the connector 140 according to the second embodiment and comparative articles. As the comparative articles, Combowire of Volcano and Certus of St Jude Medical were used. The comparative articles have a configuration in which members equivalent to the holding component 141 and the connector body 142 in the connector 140 are fixed by a screw system and do not relatively rotate (for example, refer to Japanese Unexamined Patent Application Publication (Translation of PCT Application) No. 2001-516938). In order to simulate a state where a guide wire terminal electrode is connected for the connector 140 and the comparative articles, a $\phi$0.36 mm gold-plated SUS pin having a diameter equal to that of a 0.014 mm guide wire was used as the male terminal. A 100$\Omega$ simulation resistance was connected to the proximal end side of a male terminal by soldering. The tip side of the male terminal was inserted into the female terminal, and then the contact resistance between the male terminal base end and the female terminal was evaluated.

For the evaluation of the contact resistance, an amplifier circuit containing a Wheatstone bridge was used. One amplifying and outputting a difference between the resistance (about 100$\Omega$) between the male terminal base end and the female terminal and a reference resistance of 100$\Omega$ was designed and used. For the offset adjustment, the reference resistance was slightly increased/reduced from 100$\Omega$ to be set so that the baseline was 3 V. In this amplifier circuit, a 1 V variation of an output voltage is equivalent to a 0.5$\Omega$ variation of the contact resistance. The output voltage from the amplifier circuit was recorded by a data logger (YOKOGAWA, DL850). In the above-described connection state, the movement of the guide wire assumed during an operation was simulated and a vibration and a rotation were applied to the male terminal, and then a fluctuation of amplifier circuit outputs at that time was confirmed. The results are illustrated in FIG. 21 to FIG. 23. It was confirmed in the connector 140 (FIG. 21) that the amplifier output variation (i.e., contact resistance variation) when the vibration and the rotation are given to the male terminal is further suppressed than that of the comparative articles (FIG. 22, FIG. 23). This shows a possibility of suppressing a poor contact resulting from the movement of the guide wire during an operation and a drift of sensor outputs caused by the poor contact.

Third Embodiment

<Terminal 244>

Figure 19:
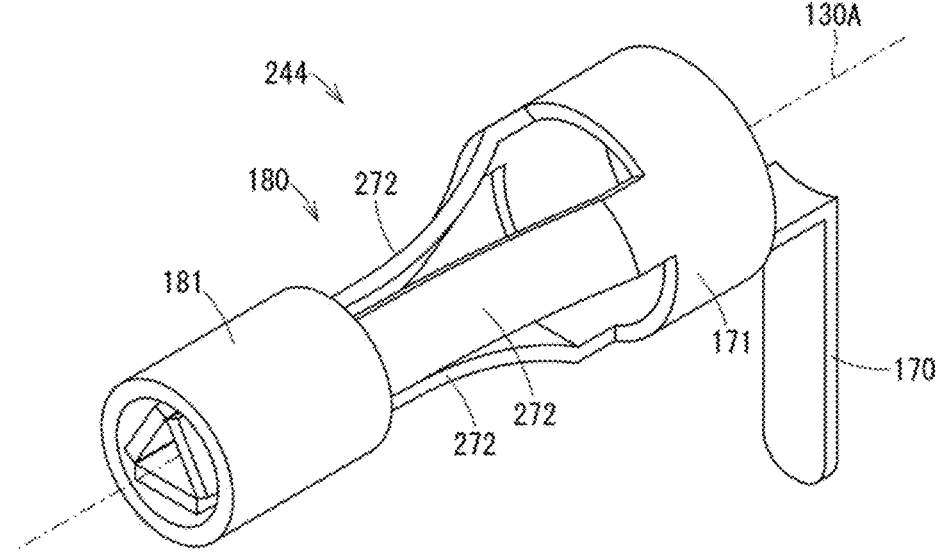
FIG. 19 is a perspective view of a terminal of a connector according to a third embodiment of the present invention.
Figure 20:
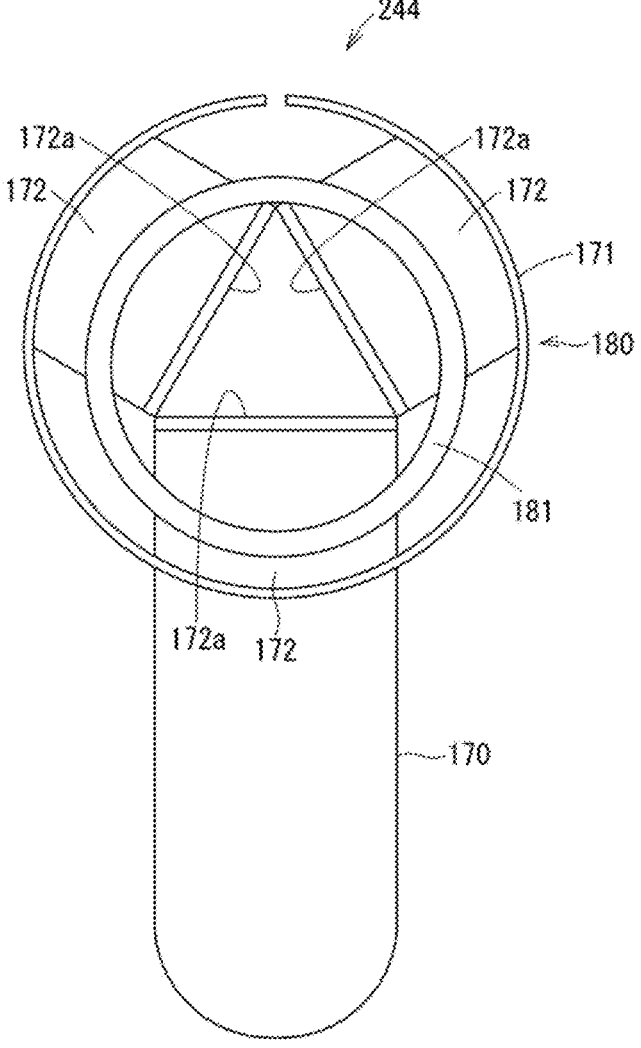
FIG. 20 is a front view of the terminal of the connector according to the third embodiment of the present invention.

A terminal 244 according to a third embodiment is described with reference to FIG. 19 and FIG. 20. A connector 140 according to the third embodiment is different from the connector 140 according to the second embodiment in the configuration of the terminal 244. The third embodiment is the same as the second embodiment other than the point. Hereinafter, the configuration of the terminal 244 according to the third embodiment is described. The members common to those of the second embodiment are designated by the same reference numerals and a description of these members is omitted.

The terminal 244 is provided with a body 180 and a converging tube 181. The body 180 is provided with the connection portion 170, the first connection portion 171, and three terminal portions 272. The material of the body 180 is metal which has conductivity and can be subjected to bending processing and is preferably spring steel. The connection portion 170, the first connection portion 171, and the three terminal portions 272, are integrally formed by performing punching and bending processing of a metal plate.

The terminal portions 272 are configured in the same manner as the terminal portions 172 according to the second embodiment except a point that one end in the axis line 130A is opened. The inner surfaces of the terminal portions 272 are contact surfaces 272a facing the contact 137 of the guide wire 130 and the contact surfaces 272a are curved so as to protrude inward in the radial direction.

The converging tube 181 is externally fitted to one end in a direction along the axis line 130A of the terminal portion 272. The shape of the converging tube 181 is a cylindrical shape. The material of the converging tube 181 is a resin material. Therefore, the converging tube 181 can be elastically deformed so as to enlarge the diameter.

One end portion of each of the terminal portions 272 is supported by the first connection portion 171 and the other end portion is supported by the converging tube 181. Therefore, the terminal portions 272 function as a plate spring when the contacts of the guide wire 130 are disposed inside the three terminal portions 272.

Operational Effects of Third Embodiment

According to the connector 140 of the third embodiment, the converging tube 181 is externally fitted to the other end of each of the terminal portions 172 and can be elastically deformed so as to enlarge the diameter. The plate spring which is the terminal portion 172 is subject to not only the energization force the plate spring itself but the energization force caused by the first connection portion 171 which is a cylindrical spring. Therefore, the energization force of the terminal portions 172 can be easily adjusted.

Modifications of Second Embodiment and Third Embodiment

The embodiments of the present invention are described above in detail but the description above is merely exemplary of the present invention in all points. It is a matter of course that various improvements or modifications can be performed without deviating from the scope of the present invention. With respect to the constituent components of the connector 140 according to each embodiment, constituent components may be omitted, replaced, and added as appropriate according to embodiments. Moreover, the shapes and the sizes of the constituent components of the connector 140 may also be set as appropriate according to embodiments. For example, the following alternations can be performed.

In the second and third embodiments, although the terminals 144 and 244 are provided with the three terminal portions 172 and 272, respectively, the present invention is not limited to the configuration. The terminals 144 and 244 may be provided with four or more of the terminal portions 172 and 272, respectively. In this case, with respect to at least three terminal portions 172 and 272 of the four or more terminal portions 172 and 272, respectively, the angle θ between the two adjacent terminal portions 172 and 272 satisfies the relationship of 90° <θ<180°.

In the second and third embodiments, although the angle θ between the two adjacent terminal portions 172 and 272 satisfies the relationship of θ=120°, the present invention is not limited to the configuration. The angle θ may be another angle insofar as the relationship of 90°<θ<180° is satisfied. The pitches (intervals) around the axis line 130A may not be equal.

In the second and third embodiments, although the shapes of the contact surfaces 172*a* and 272*a* in the cross section along the axis line 130A are curved shapes of protruding inward in the radial direction, the present invention is not limited to the configuration. The shapes of the contact surfaces 172*a* and 272*a* are not limited insofar as the shape allows the contact surfaces 172*a* and 272*a* to contact the contact 137, i.e., a shape in which the distance between the contact surfaces 172*a* and 272*a* and the axis line 130A is smaller than the radius of the contact 137 of the guide wire 130. The shapes of the contact surfaces 172*a* and 272*a* may be curved surfaces or planes extending in parallel to the axis line 130A.

In the second and third embodiments, although the shapes of the contact surfaces 172*a* and 272*a* in the cross section vertical to the axis line 130A are linear shapes, the present invention is not limited to the configuration. The shapes of the contact surfaces 172*a* and 272*a* in this cross section may be a curve protruding to the axis line 130A side or conversely a curve recessed to the axis line 130A side. In the case of the curve recessed to the axis line 130A, it is preferable that the curvature radii of the contact surfaces 172*a* and 272*a* are larger than the curvature radius of the outer surface of the contact 137 so as not to be resistance in the insertion/removal of the guide wire 130.

In the second and third embodiments, although the connector 140 is provided with the four terminals 144 and 244, the present invention is not limited to the configuration. The number of the terminals 144 and 244 may be the same as the number of the corresponding contacts 137 of the guide wire 130 and may be two, three, or five or more, for example.

In the second and third embodiments, although the proximal end side is elastically deformed inward in the radial direction with respect to the axis line 130A to slide the holding component 141 to the guide component 147 with the distal end of each of the hook portions 152 as a fulcrum, the holding component 141 and the guide component 147 may be screw-fitted to each other, and the aspect is not particularly limited. Moreover, the number of the holding pieces 151 of the holding component 141 may be one or two or more and the body 150 and the holding pieces 151 of the holding component 141 may be separate members.

In the second and third embodiments, although the lock portion 169 is provided on the inner surface of the support component 148, the support component 148 may be integrally formed with the tubular cover 145, and then the lock portion 169 may be provided on the inner surface of the integrally molded tubular cover 145 itself. Moreover, the number of the lock portions 169 may correspond to the number of the corresponding recessed portions 152*a* of the holding component 141 and may be two, three, or five or more.

In the second and third embodiments, although the connector 140 is used for the pressure sensor 111, the present invention is not limited to the pressure sensor and those capable of measuring the physical quantities of blood in a blood vessel may be acceptable. The measurement element may be a flow velocity sensor measuring the flow velocity of blood in a blood vessel, a flow volume sensor measuring the blood flow volume in a blood vessel, a temperature sensor measuring the temperature of blood, and the like, for example.

Fourth Embodiment

[Guide Wire System 310]

Figure 24:
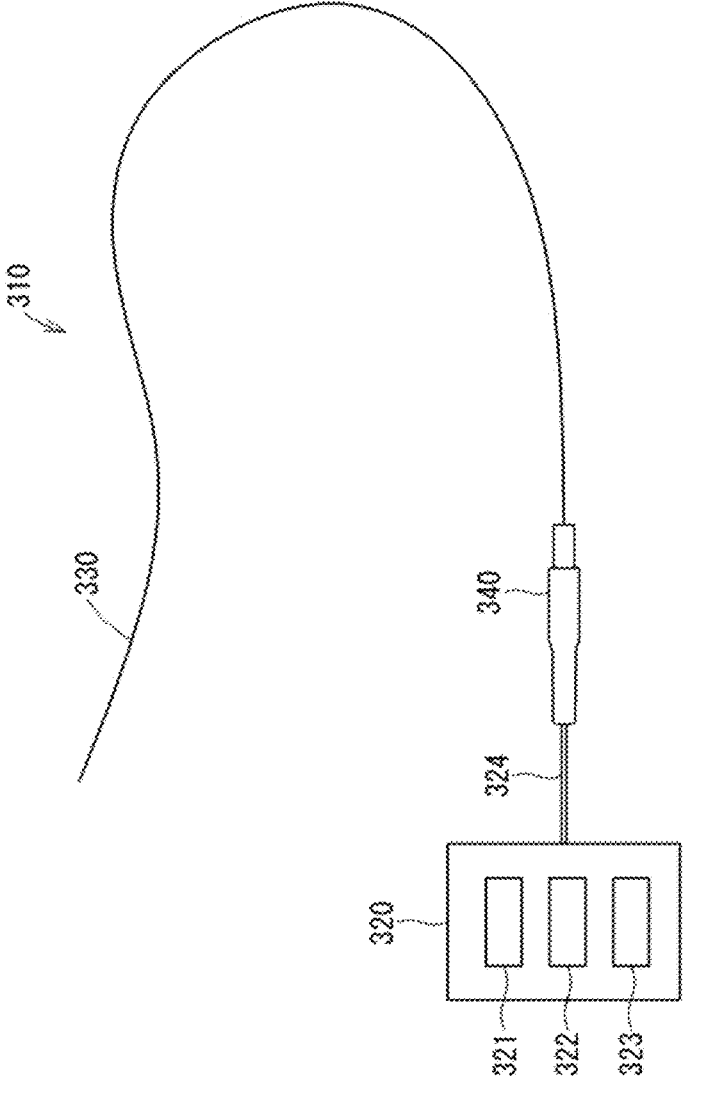
FIG. 24 is a schematic view of a guide wire system 310.

As illustrated in FIG. 24, a guide wire system 310 is provided with a guide wire 330, a calculation device 320, and a female type connector 340 connecting the guide wire 330 and the calculation device 320. The guide wire 330 is a long and narrow cable and can be inserted into blood vessels, such as coronary arteries. The guide wire 330 is provided with a pressure sensor 311 (see FIG. 26, example of the sensor) outputting electric information according to pressure in a blood vessel in a distal end portion.

The calculation device 320 is provided with a power supply portion 321 supplying a current to the pressure sensor 311 of the guide wire 330, a calculation portion 322 performing calculation processing of electric information to be output from the pressure sensor 311, and a memory 323 storing information required for the calculation processing. The electric information to be output from the pressure sensor 311 is transmitted to the calculation portion 322 via the female type connector 340 and the cable 324 from the guide wire 330. The calculation portion 322 calculates the blood pressure based on the electric information to be output from the pressure sensor 311. More specifically, the guide wire system 310 is used for the blood pressure measurement.

In FIG. 24, a fixed end (end connected to the female type connector 340) is a proximal end (end on the lower left side in FIG. 24) of both end portions of the guide wire 330 and a free end (tip when inserted in a blood vessel) thereof is a distal end (end on the upper left side in FIG. 24). In this specification, in the guide wire 30, the side on which the proximal end is present is defined as the proximal side and the side on which the distal end is present is defined as the distal side.

[Guide Wire 330]

Figure 25:
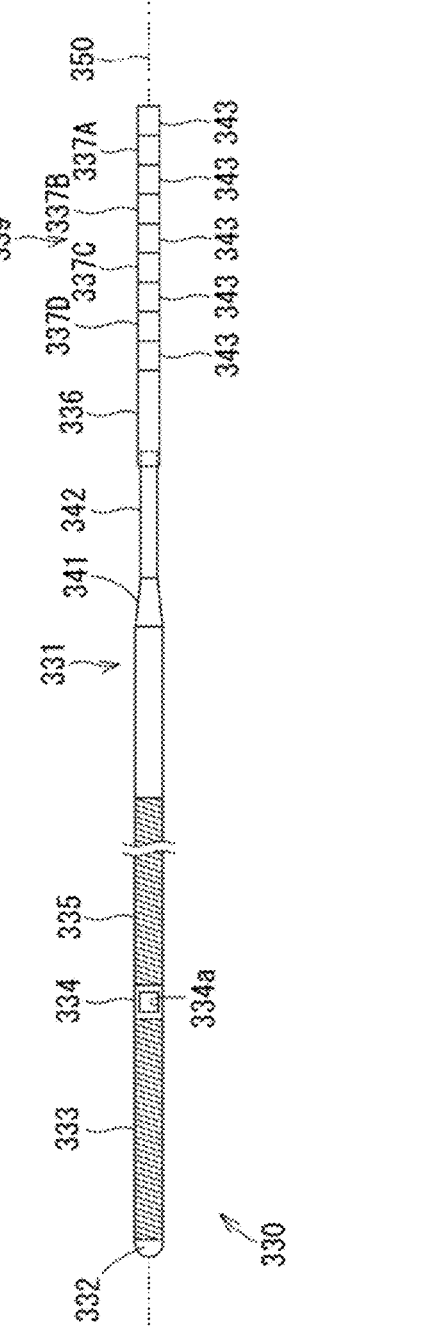
FIG. 25 is a view illustrating a guide wire 330.

FIG. 25 illustrates the guide wire 330. In FIG. 25, the left side is the distal end side of the guide wire 330 and the right side is the proximal end surface of the guide wire 330. The guide wire 330 is roughly divided into a tip portion 330A (example of the distal end), a core wire 331 (example of the body), and a male type connector 339 (example of the connector). The tip portion 330A has a tip guide portion 332, a first spiral body 333, a housing 334, and a second spiral body 335. The core wire 331 and the male type connector 339 are connected through a connection tube 336. The tip portion 330A, the core wire 331, the connection tube 336, and the male type connector 339 are linearly disposed along the axis line 350. The axis line 350 refers to the axis line of the guide wire 330 in a state where the guide wire 330 is in a straight state without being bent or curved.

The core wire 331 is a cylindrical member configuring the skeleton of the guide wire 330 and is a stainless steel tube, for example. The tip guide portion 332 is a hemispherical member which is disposed at the distal end and protrudes to the distal end side and which abuts on a blood vessel wall to thereby guide the movement direction of the guide wire 330 along the blood vessel. The first spiral body 333 and the second spiral body 335 are spirally wound wire rods and configured so as to be easier to bend than the core wire 331 so that a distal end portion of the guide wire 330 easily moves along the blood vessel.

The housing 334 is a casing accommodating the pressure sensor 311 (example of the electronic component) in the internal space. The housing 334 has two through-holes 334a. The two through-holes 334a are 180° symmetrically disposed with respect to the axis line 350. FIG. 24 illustrates only one through-hole 334a. Blood enters the housing 334 through the through-holes 334a to contact a diaphragm 313 (FIG. 26) of the pressure sensor 311.

A tapered pin 338 extends in the internal space of the second spiral body 335 toward the housing 334 from the distal end of the core wire 331. The tapered pin 338 is a member reinforcing the bending rigidity of the second spiral body 335. The tapered pin 338 has a cylindrical shape and the outer diameter gradually decreases toward the housing 334 from the distal end of the core wire 331. Although not illustrated in each figure, a tip guide pin extends in the internal space of the first spiral body 333 toward the tip guide portion 332 from the distal end of the housing 334. The tip guide pin is a member having a cylindrical shape and reinforcing the bending rigidity of the first spiral body 333. The tip guide pin is fixed to the housing 334 and the tip guide portion 332.

Figure 26:
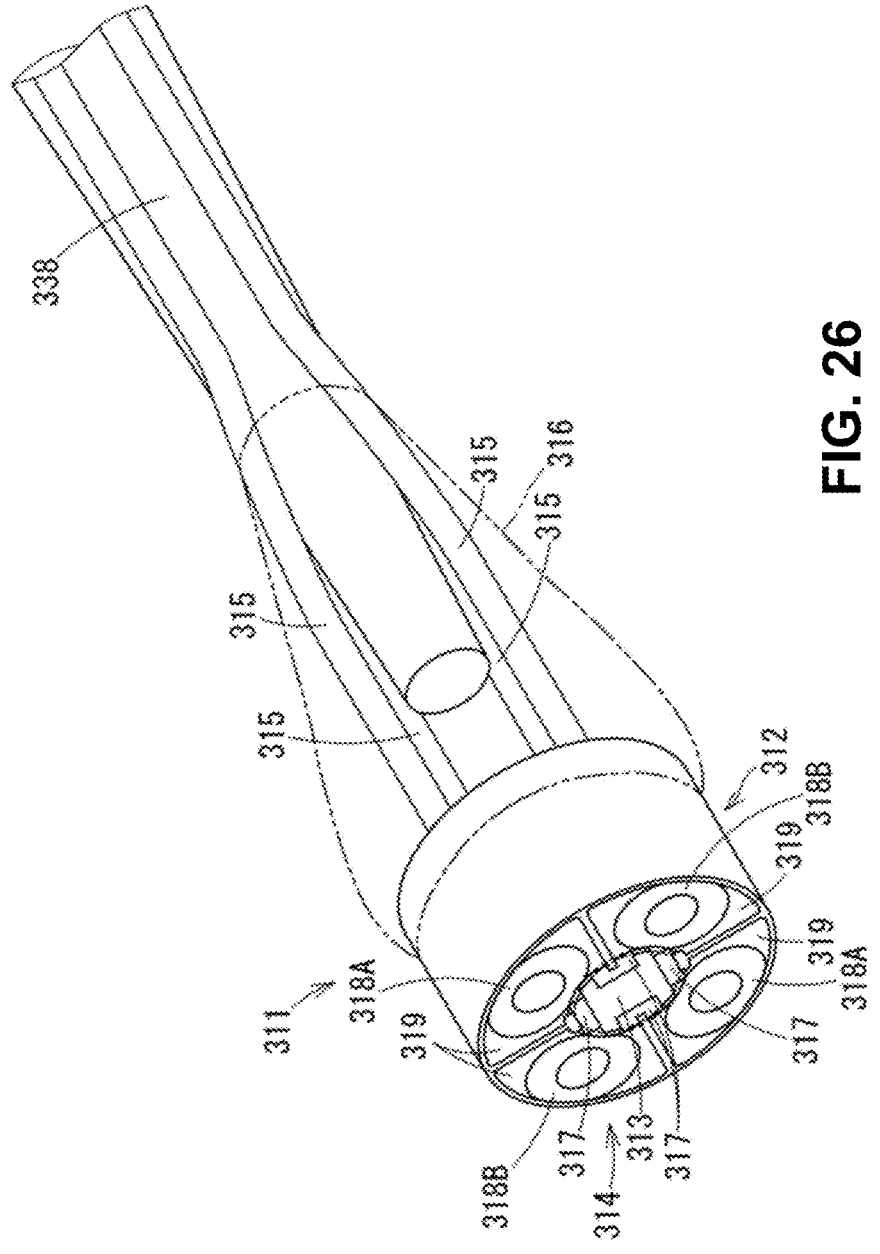
FIG. 26 is a perspective view of a pressure sensor 311.

As illustrated in FIG. 26, the pressure sensor 311 is provided with a sensor body 312, the diaphragm 313, a bridge circuit 314, four conductive wires 315, and a connection portion 316. The sensor body 312 is fixed to the tapered pin 338 fixed to the core wire 331 by the connection portion 316 containing an adhesive, for example. To the sensor body 312, the diaphragm 313, the bridge circuit 314, and the four conductive wires 315 are attached. The bridge circuit 314 is a full bridge circuit in which four resistors 317 all function as a distortion gauge for measurement. The bridge circuit 314 is provided with the four resistors 317, four terminals 318A and 318B, and four connection bodies 319. The four resistors 317 are fixed to the diaphragm 313. The four terminals 318A and 318B contain two input terminals 318A and two output terminals 318B. Each of the connection bodies 319 electrically connects each of the resistors 317 to each of the terminals 318A and the terminals 318B. Each of the conductive wires 315 is electrically connected to each of the terminals 318A and 318B and extends toward the proximal end in the internal space of the core wire 331.

In a state where the guide wire 330 is inserted into a blood vessel, so that blood pressure is applied to the pressure sensor 311, the diaphragm 313 is elastically deformed according to the blood pressure. The four resistors 317 are elastically deformed with the elastic deformation of the diaphragm 313, so that the electrical resistance values of the four resistors 317 vary. When a voltage is applied between the two input terminals 318A in this state, a potential difference is generated between the two output terminals 318B. Based on the potential difference, the blood pressure is calculated in the calculation device 320 (FIG. 24).

Figure 27:
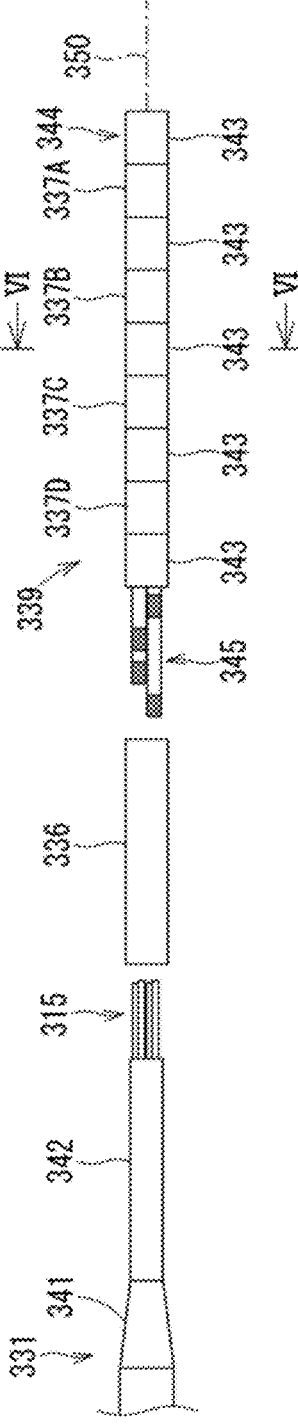
FIG. 27 is an exploded view of a male type connector 339.

As illustrated in FIG. 27, a tapered portion 341 in which the outer diameter decreases toward the proximal end and a small-diameter portion 342 extends from the tapered portion 341 to the proximal end are formed in a proximal end portion of the core wire 331. The outer diameter of the small-diameter portion 342 is smaller than the outer diameter of the core wire 331 in the distal end relative to the tapered portion 341 and is a fixed outer diameter along the axis line 350. The length along the axis line 350 of the small-diameter portion 342 is longer than the length along the axis line 350 of the connection tube 336. The proximal end of the core wire 331 is opened and the four conductive wires 315 inserted into and passed through the internal space of the core wire 331 extend to the outside from the opening of the proximal end.

As illustrated in FIGS. 25 and 27, the connection tube 336 connects a proximal end portion of the core wire 331 and a distal end portion of the male type connector 339. The connection tube 336 is a tube containing conductive materials, such as stainless steel, for example, and the proximal end and the distal end are individually opened. The outer diameter of the connection tube 336 is almost equal to the outer diameter on the distal end side relative to the tapered portion 341 of the core wire 331. The inner diameter of the connection tube 336 is almost equal to the outer diameter of the small-diameter portion 342 of the core wire 331. The inner surface of the connection tube 336 contacts the outer surface of the small-diameter portion 342, whereby the connection tube 336 and the core wire 331 are electrically connected. In a state where the connection tube 336 is not fixed to the small-diameter portion 342 with an adhesive or the like, the connection tube 336 is movable along the axis line 350 with respect to the small-diameter portion 342. In a state where the connection tube 336 is fixed to the small-diameter portion 342, the connection tube 336 covers the four conductive wires 315 extending from the proximal end of the core wire 331.

As illustrated in FIGS. 25 and 27, the male type connector 339 is obtained by inserting four electrode pins 345 into the internal space of a complex 344 of a cylindrical tube shape in which four electrode rings 337A, 337B, 337C, and 337D and five insulation rings 343 are alternately connected.

The electrode rings 337A, 337B, 337C, and 337D have a cylindrical shape and conductivity which allows the conduction between the inner surface and the outer surface. The electrode rings 337A, 337B, 337C, and 337D may be those formed of a conductive member, for example, or may be those obtained by plating the surface of a cylindrical member with a conductive member. The insulation rings 343 are those having a cylindrical shape and containing insulating materials, such as polyimide. The inner diameter and the outer diameter of the electrode rings 337A, 337B, 337C, and 337D and the inner diameter and the outer diameter of the insulation rings 343 are equal to each other, respectively. The complex 344 of the cylindrical tube shape is formed by individually disposing the electrode rings 337A, 337B, 337C, and 337D between the five insulation rings 343, and then integrally fixing them. The length along the axis line 350 of each of the electrode rings 337A, 337B, 337C, and 337D and each of the insulation rings 343 may be the same or may be different from each other, for example. The outer diameter of the complex 344 is almost equal to the outer diameter of the connection tube 336.

Figure 28:
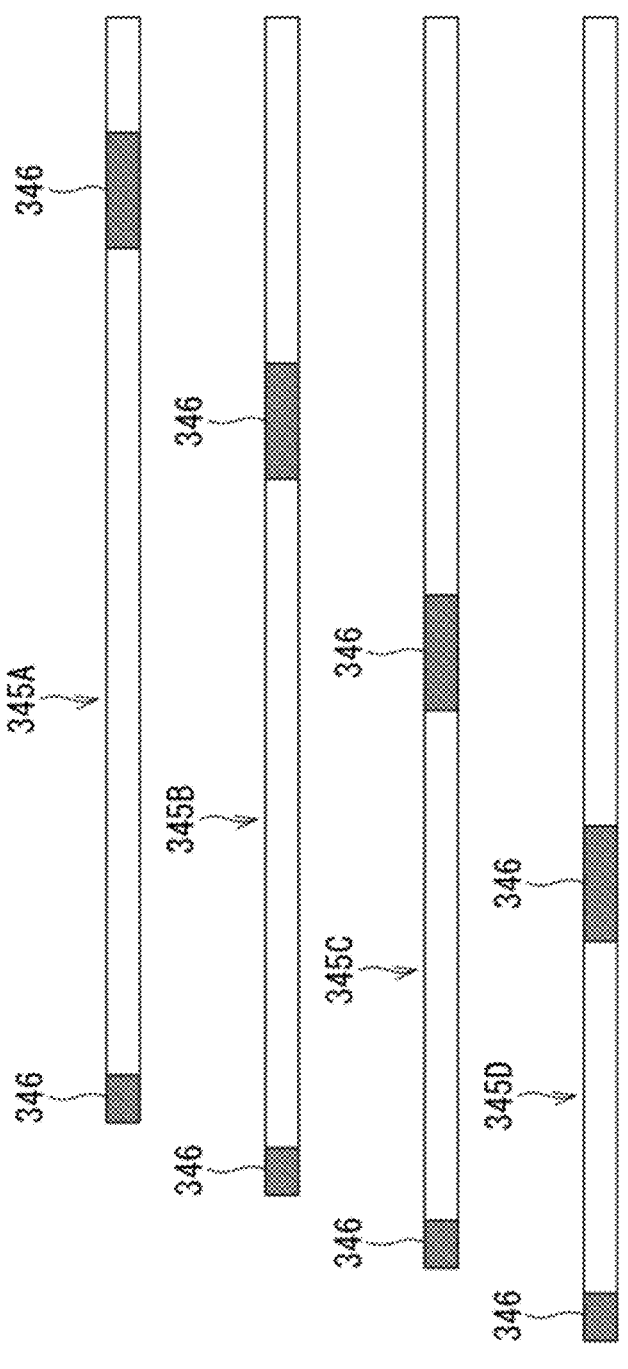
FIG. 28 is a view illustrating each of the electrode pins 345.

As illustrated in FIG. 28, the four electrode pins 345A, 345B, 345C, and 345D are columnar members different in the length along the axis line 350. The four electrode pins 345A, 345B, 345C, and 345D are those containing conductive materials or those having a surface plated with a conductive member and those having an insulation-coated outermost surface. The outer diameters of the four electrode pins 345A, 345B, 345C, and 345D are equal to each other. In this specification, when a description is given while not particularly distinguishing the four electrode pins 345A, 345B, 345C, and 345D from each other, the four electrode pins 345A, 345B, 345C, and 345D are merely simply referred to as "electrode pins 345".

As illustrated in FIG. 28, distal end portions of the four electrode pins 345A, 345B, 345C, and 345D are conduction portions 346 not having the insulation coat. The conduction portions 346 are connected to the conductive wires 315 in one-to-one correspondence. In the state where the four electrode pins 345A, 345B, 345C, and 345D are arranged while aligning the positions in a direction along the axis line 350 of the proximal end portions as illustrated in the figure, the positions in a direction along the axis line 350 of the conduction portions 346 of the distal end portions (conduction portions 346 located on the left side in FIG. 28) do not overlap with each other.

The four electrode pins 345A, 345B, 345C, and 345D each have the two conduction portions 346. The electrode pin 345A with the shortest length along the axis line 350 among the four electrode pins has the conduction portion 346 not having the insulation coat at a position somewhat apart from a proximal end portion (end portion on the right side in FIG. 28). The conduction portion 346 on the proximal end side of the electrode pin 345A corresponds to a position in a direction along the axis line 350 of the electrode ring 337A located on the most proximal end side in the complex 344.

The electrode pin 345B having the next shortest length has the conduction portion 346 at a position apart from the proximal end. The conduction portion 346 on the proximal end side of the electrode pin 345B corresponds to a position in the direction along the axis line 350 of the second electrode ring 337B from the proximal end in the complex 344. In the state illustrated in FIG. 28, the positions in the direction along the axis line 350 (horizontal direction in FIG. 28) of the conduction portion 346 on the proximal end side of the electrode pin 345A and the conduction portion 346 on the proximal end side of the electrode pin 345B do not overlap with each other.

Similarly, the conduction portion 346 on the proximal end side in the electrode pin 345C having the third shortest length corresponds to the position in the direction along the axis line 350 of the third electrode ring 337C from the proximal end in the complex 344. The conduction portion 346 on the proximal end side in the longest electrode pin 345D corresponds to the position in the direction along the axis line 350 of the fourth electrode ring 337D from the proximal end in the complex 344. In the state illustrated in FIG. 28, the positions in the direction along the axis line 350 of the conduction portions 346 of the four electrode pins 345A, 345B, 345C, and 345D do not overlap with the positions of the other conduction portions 346.

As illustrated in FIG. 27, the four electrode pins 345A, 345B, 345C, and 345D are inserted into the internal space of the complex 344 in a state where the positions of the proximal ends are aligned with each other. The distal end portions of the four electrode pins 345A, 345B, 345C, and 345D extend to the outside from the distal end of the complex 344 and the conduction portions 346 on the distal end side are exposed to the outside. In the state where the four electrode pins 345A, 345B, 345C, and 345D are inserted into the internal space of the complex 344, the positions in the direction along the axis line 350 of the distal ends are different from each other.

Figure 29:
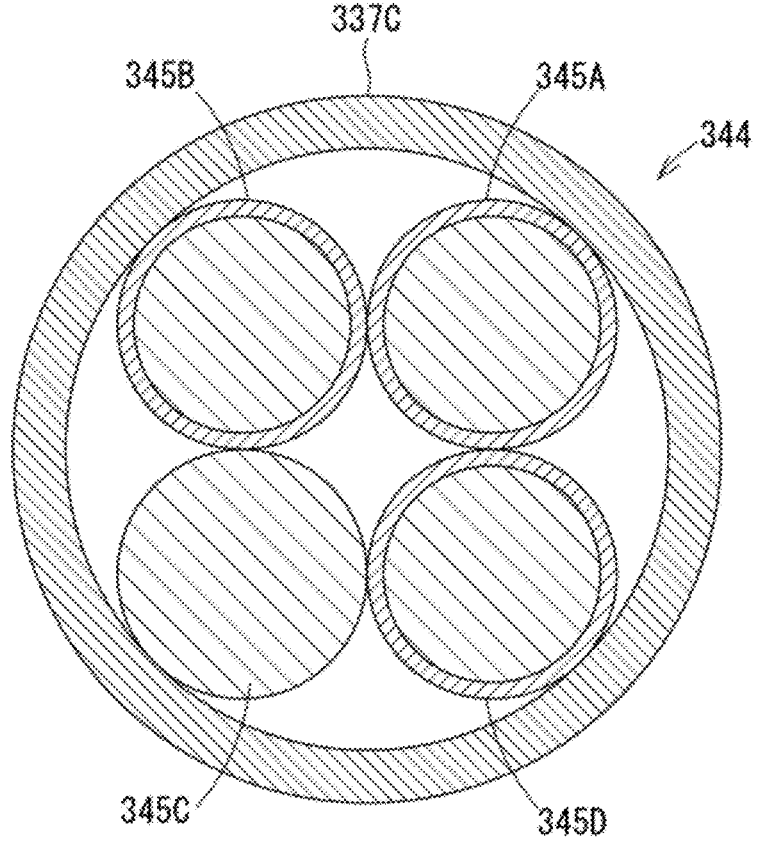
FIG. 29 is a cross-sectional view along the cut line VI-VI of FIG. 27.

As illustrated in FIG. 29, the four electrode pins 345A, 345B, 345C, and 345D are disposed so as to be different in the position in the circumferential direction in the internal space of the complex 344. More specifically, the four electrode pins 345A, 345B, 345C, and 345D are in a state of being bundled into one. The four electrode pins 345A, 345B, 345C, and 345D individually abut on the inner surface of the complex 344 and individually abut on the other two electrode pins 345. Thus, the four electrode pins 345A, 345B, 345C, and 345D are stably disposed in the internal space of the complex 344. Although not illustrated in the figure, a columnar shaped core material abutting on each of the four electrode pins 345A, 345B, 345C, and 345D may be disposed at the center (position of the axis line 350) of the complex 344.

As illustrated in FIG. 29, the conduction portion 346 on the proximal end side of the third shortest electrode pin 345C contacts the inner surface of the third electrode ring 337C and is made electrically conductive by being fixed by soldering or the like in the third electrode ring 337C from the proximal end in the complex 344. The outer peripheral surfaces of the other electrode pins 345A, 345B, and 345D are insulation-coated, and thus are insulated although abutting on the third electrode ring 337C. Thus, the conduction portions 46 on the proximal end side of the four electrode pins 345A, 345B, 345C, and 345D are electrically connected to the electrode rings 337A, 337B, 337C, and 337D in one-to-one correspondence.

[Method for Manufacturing Guide Wire 330]

Hereinafter, a method for manufacturing the guide wire 330 and particularly a method for connecting the core wire 331 and the male type connector 339 are described.

The four conductive wires 315 extend from the proximal end of the core wire 331 to which the pressure sensor 311 and the like are assembled beforehand. The male type connector 339 is assembled in the state where the four electrode pins 345A, 345B, 345C, and 345D are inserted into the internal space of the complex 344 and the conduction portions 346 are individually connected to the electrode rings 337A, 337B, 337C, and 337D.

[First Process]

Figure 30:
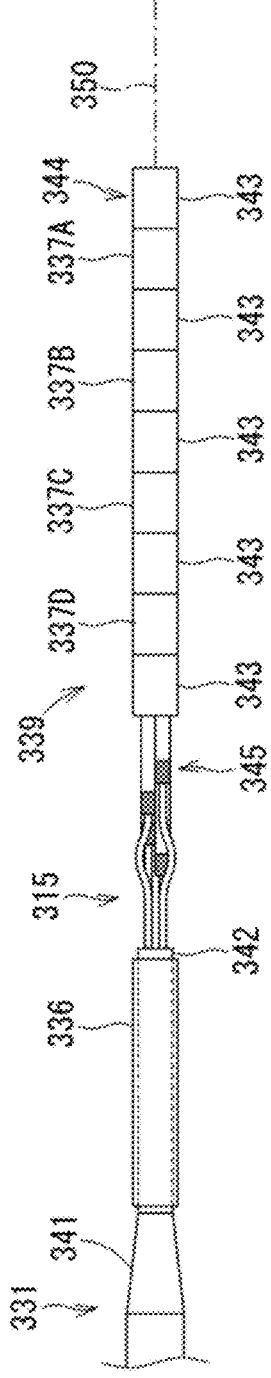
FIG. 30 is a view illustrating the guide wire 330 when a connection tube 336 is in an externally fitted state.

As illustrated in FIG. 30, an externally fitted state is formed in which the connection tube 336 is externally fitted to the small-diameter portion 342 of the core wire 331, and then moved to the most distal end side. In the externally fitted state, the connection tube 336 does not project in the direction along the axis line 350 from the proximal end of the small-diameter portion 342 or, even when projecting, slightly projects. Moreover, in the externally fitted state, the four conductive wires 315 extend to the outside from the proximal end portion of the connection tube 336. In the externally fitted state, the conductive wires 315 and the electrode pins 345 are electrically connected by soldering or the like. The conductive wires 315 can be distinguished from each other by classifying the insulation coats by color, for example. Moreover, the electrode rings 337A, 337B, 337C, and 337D to which the electrode pins 345 are connected can be distinguished from each other based on the positions of the distal ends projecting from the complex 344.

[Second Process]

After the conductive wires 315 and the electrode pins 345 are electrically connected, the connection tube 336 in the externally fitted state is moved so as to project in the direction along the axis line 350 from the small-diameter portion 342 of the core wire 331. Thus, connection portions between the conductive wires 315 and the conduction portions 346 of the electrode pins 345 are covered with the connection tube 336, and a proximal end portion of the connection tube 336 contacts the male type connector 339 as illustrated in FIG. 25. Then, the connection tube 336 is connected by being fixed to the small-diameter portion 342 of the core wire 331 and the male type connector 339 by an adhesive or the like.

Operational Effects of Fourth Embodiment

According to the guide wire 330, the conduction portions 346 of the electrode pins 345 project outward from the distal end of the complex 344 even when the male type connector 339 is an assembly article beforehand, and therefore the conduction portions 346 and the conductive wires 315 are easily connected. Moreover, even when a trouble arises in the connection process of the conduction portions 346 and the conductive wires 315, only the male type connector 339 may be exchanged, and therefore the productivity is good.

Moreover, the electrode pins 345 are disposed at the different positions in the circumferential direction in the internal space of the complex 344, and therefore the strength of the male type connector 339 is held due to the fact that the electrode pins 345 are bundled in the internal space of the complex 344.

Moreover, the conduction portions 346 on the distal side end side of the electrode pins 345 accommodated in the internal space of the complex 344 are different in the position in the direction along the axis line 350, and therefore the connection relationship between the electrode pins 345 and the electrode rings 337A, 337B, 337C, and 337D can be easily grasped based on the positions of the conduction portion 346.

Moreover, the electrode pins 345 have the insulation coated outermost surfaces and have the conduction portions 346 in the distal end portions and at the positions individually corresponding to the electrode rings 337A, 337B, 337C, and 337D to be connected and the conduction portions 346 do not overlap in the direction along the axis line 350 in the male type connector 339. Therefore, a short circuit between the conduction portions 346 of the electrode pins 345 can be suppressed.

Moreover, the connection tube 336 covering the connection portions between the conductive wires 315 and the electrode pins 345 is configured as a separate component from the core wire 331 and the male type connector 339. Therefore, no member covers the conductive wires 315 and the conduction portions 346 of the electrode pins 345 in the state where the connection tube 336 is not connected to the core wire 331 and the male type connector 339, and thus an operation of electrically connecting the conductive wires 315 and the conduction portions 346 of the electrode pins 345 is easily performed.

Moreover, the small-diameter portion 342 is provided in a distal end portion of the core wire 331 and the connection tube 336 is movable in the direction along the axis line 350 with respect to the small-diameter portion 342. Therefore, the conductive wires 315 and the conduction portions 346 of the electrode pins 345 are easily exposed to the outside or covered by the movement of the connection tube 336.

Moreover, the outer diameter of the connection tube 336 and the outer diameter on the distal end side relative to the tapered portion 341 of the core wire 331 can be equalized to each other.

Moreover, the connection tube 336 is one containing a conductive material and is electrically connected to the core wire 331, and therefore the core wire 331 can be easily grounded through the connection tube 336.

According to the method for manufacturing the guide wire 330 in the fourth embodiment, the conductive wires 315 and the conduction portions 346 of the electrode pins 345 are connected in the state where the connection tube 336 is not connected to the core wire 331 and the male type connector 339. Therefore, there is no member covering the conductive wires 315 and the conduction portions 346 of the electrode pins 345, and thus the workability is good.

Moreover, by the movement of the connection tube 336 from the externally fitted state with respect to the small-diameter portion 342 of the core wire 331, the conductive wires 315 and the conduction portions 346 of the electrode pins 345 are easily exposed to the outside or covered.

Modification of Fourth Embodiment

In the method for manufacturing the guide wire 330 in the fourth embodiment described above, although the connection tube 336 is externally fitted to the small-diameter portion 342 of the core wire 331 in the externally fitted state, a state where the connection tube 336 is externally fitted to the male type connector 339 in place of the small-diameter portion 342 may be an externally fitted state. In the case of the externally fitted state, the inner diameter of the connection tube 336 is almost equal to the outer diameter of the male type connector 339. After the conductive wires 315 and the conduction portions 346 of the electrode pins 345 are connected, the connection tube 336 in the externally fitted state is moved so as to project in the direction along the axis line 350 from the male type connector 339.

Moreover, in the method for manufacturing the guide wire 330 in the fourth embodiment described above, the conductive wires 315 and the conduction portions 346 of the electrode pins 345 may be connected in a state where the connection tube 336 is not brought into the externally fitted state and is not externally fitted to the guide wire 330 nor the male type connector 339. Thereafter, the connection tube 336 may be moved to the distal end portion while being externally fitted to a proximal end portion of the male type connector 339, for example, so that the connection tube 336 may be externally fitted to and connected to the small-diameter portion 342 of the core wire 331 and the male type connector 339.

Moreover, the connection tube 336 is not an indispensable configuration in the guide wire 330 and the guide wire 330 which does not have the connection tube 336 may be configured. For example, the proximal end of the core wire 331 and the male type connector 339 may be directly connected. In that case, the conductive wires 315 extending from the proximal end of the core wire 331 are connected to the conduction portions 346 of the corresponding electrode pins 345, so that the conductive wires 315 are accommodated in a deflected state in the internal space of the core wire 331.

Moreover, the number of the conductive wires 315, the number of the electrode rings 337A, 337B, 337C, and 337D, and the number of the electrode pins 345 in the fourth embodiment described above are merely exemplary and the number of the conductive wires 315, the number of the electrode rings 337A, 337B, 337C, and 337D, and the number of the electrode pins 345 may be one or arbitrarily two or more.

Moreover, the pressure sensor 311 provided in the guide wire 330 is merely an example of the electronic component and the other sensors measuring the physical quantities (temperature, flow velocity, and the like) of blood or a blood vessel other than the pressure or electronic circuits may be provided. Moreover, the configuration of the distal side end of the guide wire 330 described in the fourth embodiment described above is merely an example. It is a matter of course that the configurations of the spiral body, the tapered pin, the housing, and the like may be altered as appropriate.

REFERENCE SIGNS LIST

10 pressure measuring device
11 pressure sensor
12 sensor body
12a distal end surface
12b proximal end surface
13 diaphragm
14 bridge circuit
15 conductive wire
16 coating member
17 resistor
17A first resistor
17B second resistor
18 terminal
18A, 18C input terminal
18B, 18D output terminal
22 through-hole
24 distal electroconductive layer (portion laminated on distal end surface of electroconductive layer)
26 connection portion
30 guide wire
30A axial direction
31 core wire
34 housing
39 tapered pin
110 guide wire system
111 pressure sensor
130 guide wire
130A axis line
135 second spiral body
137 contact
140 connector
141 holding component (example of holding portion)
142 connector body
143 cable
144, 244 terminal
147 guide component (example of guide portion)
148 support component (example of support portion)
150 body
150a insertion hole
151 holding piece
153 fitting portion
165a guide surface
169 lock portion
172, 272 terminal portion
172a, 272a contact surface
180 body
181 converging tube
θ angle
311 pressure sensor (electronic component)
315 conductive wire
330 guide wire

40

331 core wire (body)
336 connection tube
337A, 337B, 337C, 337D electrode ring
339 male type connector
341 tapered portion
342 small-diameter portion
345 electrode pin
346 conduction portion

The invention claimed is:

1. A guide wire connector comprising:
a support member;
a holding member configured to hold a guide wire and to rotate around an axis line of the guide wire with respect to the support member;
a guide member configured to rotate around the axis line with respect to the support member; and
a terminal electrically connected to a contact of the guide wire, wherein
the guide wire connector is changeable between a locked state and an unlocked state;
the holding member has:
a body having an insertion hole for the guide wire;
holding pieces each extending from the body in an axial direction of the guide wire, and configured to be elastically deformed inward in a radial direction of the guide wire;
a hook portion integrally molded with the body, the hook portion configured to be elastically deformed inward in the radial direction; and
a fitting portion configured to be fitted to the guide member in the locked state;
the guide member has:
a guide surface configured to guide the holding pieces inward in the radial direction; and
a fitting target portion to be fitted to the fitting portion in the locked state;
the support member has:
a second body having a cylindrical shape; and
a ring-shaped protruding portion protruding from an inner circumferential surface of the second body inward in the radial direction, the ring-shaped protruding portion configured, in the locked state, to prevent axial movement of the holding member relative to the support member while allowing the holding member to rotate with respect to the support member;
the hook portion has a recessed portion in a proximal end portion of the hook portion, the recessed portion configured to engage with the ring-shaped protruding portion;
the holding member is attached to the support member so that the holding pieces are positioned in an internal space of the guide member and the fitting portion is positioned on a proximal side of the ring-shaped protruding portion;
the holding member is configured to be movable in the axial direction with respect to the guide member in a state where the holding member is attached to the support member between a first position where the fitting portion is fit to the fitting target portion and a second position where the fitting portion abuts on the ring-shaped protruding portion;
when the holding member is in the first position, the guide wire connector is in the locked state in which the ring-shaped protruding portion engages with the recessed portion, the holding pieces abut on the guide surface to be elastically deformed inward in the radial direction so as to hold the guide wire, and the holding member and the guide member rotate together with respect to the support member; and when the holding member is in the second position, the guide wire connector is in the unlocked state in which the ring-shaped protruding portion does not engage with the recessed portion, the holding pieces do not hold the guide wire, and the guide member does not rotate with respect to the support member even when the holding member rotates with respect to the support member.

2. The guide wire connector according to claim 1, wherein the terminal has at least three terminal portions disposed around the axis line, and the at least three terminal portions individually abut on the contact while being elastically displaced outward in the radial direction.

3. The guide wire connector according to claim 2, wherein each of the terminal portions has a contact surface facing the contact, and a cross section of the contact surface along the axis line has a curved shape protruding inward in the radial direction.

4. The guide wire connector according to claim 2, wherein each of the terminal portions is a plate spring, and the terminal has a shape in which each of first ends and second ends of the plate springs in the axial direction integrally continues in a cylindrical shape along a circumferential direction, respectively.

5. The guide wire connector according to claim 2, wherein each of the terminal portions is a plate spring, and the terminal has a shape in which first ends of the plate springs in the axial direction integrally continue in a cylindrical shape along a circumferential direction, and a converging tube externally fitted to second ends of the plate springs is provided, the converging tube configured to be elastically deformed so as to enlarge a diameter of the converging tube.

6. The guide wire connector according to claim 1, wherein an angle θ around the axis line between two adjacent terminal portions satisfies a relationship of 90°<θ<180°.

7. The guide wire connector according to claim 6, wherein the angle θ satisfies a relationship of θ=120°.

8. The guide wire connector according to claim 1, further comprising:

a terminal case configured to accommodate the terminal; and a tubular cover housing the terminal case, the guide member, the support member, and at least a proximal portion of the holding member; and wherein the guide surface tapers inward toward a proximal end of the guide member, and proximal to the guide surface the guide member has a first tubular portion having a wider diameter than a proximal end of the guide surface;

wherein the terminal case has two concentric tubular portions at a distal end, the first tubular portion of the guide member mating with an outer one of the two concentric tubular portions of the terminal case, an inner one of the two concentric tubular portions having a smaller diameter than the first tubular portion of the guide member and mating into the first tubular portion of the guide member;

wherein the first tubular portion of the guide member and the outer one of the two concentric tubular portions of the terminal case are configured to fix an axial position of the proximal end of the guide member relative to the terminal case.

9. The guide wire connector according to claim 8, in which the guide member extends axially, comprising:

the first tubular portion at the proximal end of the guide member;

a third portion spanning full length of the guide surface; and a second tubular portion distal to the third portion; and wherein the first tubular portion has an outer diameter wider than a widest outer diameter of the third portion and the second tubular portion has an outer diameter wider than the widest outer diameter of the third portion; and the support member is fitted to a distal end of the second tubular portion.

* * * * *